United States Patent
Kraus et al.

(10) Patent No.: US 11,529,344 B2
(45) Date of Patent: Dec. 20, 2022

(54) EZH2 INHIBITOR COMBINATION THERAPIES

(71) Applicant: Pfizer Inc., New York, NY (US)

(72) Inventors: Manfred Kraus, San Diego, CA (US); Pei-Pei Kung, San Diego, CA (US); Thomas Andrew Paul, San Diego, CA (US); Shikhar Sharma, San Diego, CA (US); Dominique Verhelle, Boston, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/762,388

(22) PCT Filed: Nov. 9, 2018

(86) PCT No.: PCT/IB2018/058795
§ 371 (c)(1),
(2) Date: May 7, 2020

(87) PCT Pub. No.: WO2019/097369
PCT Pub. Date: May 23, 2019

(65) Prior Publication Data
US 2020/0268740 A1    Aug. 27, 2020

Related U.S. Application Data

(60) Provisional application No. 62/739,990, filed on Oct. 2, 2018, provisional application No. 62/684,832, filed
(Continued)

(51) Int. Cl.
*A61K 31/4725* (2006.01)
*A61P 35/00* (2006.01)
(Continued)

(52) U.S. Cl.
CPC ........ *A61K 31/4725* (2013.01); *A61K 31/357* (2013.01); *A61K 31/4412* (2013.01);
(Continued)

(58) Field of Classification Search
CPC .............. A61K 2300/00; A61K 31/282; A61K 31/357; A61K 31/4545; A61K 31/4709;
(Continued)

(56) References Cited

U.S. PATENT DOCUMENTS 9,040,515 B2   5/2015   Edwards et al.
9,481,666 B2   11/2016  Kania et al.
(Continued)

FOREIGN PATENT DOCUMENTS

WO   2011/140324   11/2011
WO   2011/140325   11/2011
(Continued)

OTHER PUBLICATIONS

S. Peters S. Peters et al. (Anals of Oncology, vol. 28, Supplement 2, Apr. 2017).*
(Continued)

*Primary Examiner* — Sabiha N Qazi
(74) *Attorney, Agent, or Firm* — Zhigang Rao

(57) ABSTRACT

This invention relates to combination therapies comprising an EZH2 inhibitor and a chemotherapeutic agent, and associated pharmaceutical compositions, methods of treatment, and pharmaceutical uses.

8 Claims, 22 Drawing Sheets

Related U.S. Application Data on Jun. 14, 2018, provisional application No. 62/628,314, filed on Feb. 9, 2018, provisional application No. 62/585,781, filed on Nov. 14, 2017.

(51) Int. Cl.

| | |
|---|---|
| *A61K 33/243* | (2019.01) |
| *A61K 31/357* | (2006.01) |
| *A61K 31/4412* | (2006.01) |
| *A61K 31/4433* | (2006.01) |
| *A61K 31/4545* | (2006.01) |
| *A61K 31/496* | (2006.01) |
| *A61K 31/501* | (2006.01) |
| *A61K 31/5355* | (2006.01) |
| *A61K 39/395* | (2006.01) |
| *A61K 45/06* | (2006.01) |

(52) U.S. Cl.
CPC ...... *A61K 31/4433* (2013.01); *A61K 31/4545* (2013.01); *A61K 31/496* (2013.01); *A61K 31/501* (2013.01); *A61K 31/5355* (2013.01); *A61K 33/243* (2019.01); *A61K 39/3955* (2013.01); *A61K 45/06* (2013.01); *A61P 35/00* (2018.01)

(58) Field of Classification Search
CPC .............. A61K 31/496; A61K 31/501; A61K 31/5377; A61K 31/4412; A61K 31/4433; A61K 31/4725; A61K 31/5355; A61K 33/243; A61K 39/3955; A61K 45/06; A61K 9/0019; A61P 35/00
USPC ........................................................ 514/649
See application file for complete search history.

(56) References Cited

U.S. PATENT DOCUMENTS

| | | | |
|---|---|---|---|
| 10,246,433 | B2 | 4/2019 | Edwards et al. |
| 10,570,121 | B2 | 2/2020 | Collins et al. |

FOREIGN PATENT DOCUMENTS

| | | |
|---|---|---|
| WO | 2012/005805 | 1/2012 |
| WO | 2012/034132 | 3/2012 |
| WO | 2012/068589 | 5/2012 |
| WO | 2012/118812 | 9/2012 |
| WO | 2012/142504 | 10/2012 |
| WO | 2012/142513 | 10/2012 |
| WO | 2013/049770 | 4/2013 |
| WO | 2013/120104 | 8/2013 |
| WO | 2013/173441 | 11/2013 |
| WO | 2014/049488 | 4/2014 |
| WO | 2014/097041 | 6/2014 |
| WO | 2014/062720 | 8/2014 |
| WO | 2014/124418 | 8/2014 |
| WO | 2015/193765 | 12/2015 |
| WO | 2017/132518 | 8/2017 |
| WO | 2017/192290 | 11/2017 |

OTHER PUBLICATIONS

Rossi A, Di Maio M. Platinum-based chemotherapy in advanced non-small-cell lung cancer: optimal number of treatment cycles. Expert Rev Anticancer Ther. Jun. 2016;16(6):653-60. doi: 10.1586/14737140.2016.1170596. Epub Apr. 8, 2016. PMID: 27010977.*
Sequist et al. (Annals of Oncology 27 (Supplement 6); vi493-vi496, 2016, Clinical activity, safety and predictive biomarkers results from a phase 1a atezolizumab (atezo) trial in extensive-stage small cell lung cancer (ES-SCLC), abstract, attached with this office action).*
Gardner et al., "Chemosensitive Relapse in Small Cell Lung Cancer Proceeds through an EZH2-SLFN11 Axis", Cancer Cell, vol. 31(2), pp. 286-299, Feb. 13, 2017.
Kung et al., J. Med. Chem., vol. 59, pp. 8306-8325 (2016).
Fillmore et al., "EZH2 inhibition sensitizes BRG1 and EGFR mutant lung tumours to TopoII inhibitors", Nature, vol. 520(7546), pp. 239-242 (2015).
Kung et al., "Optimization of Orally Bioavailable Enhancer of Zeste Homolog 2 (HZH2) Inhibitors Using Ligand and Property-Based Design Strategies: Identification of Development Candidate (R)-5,8-Dichloro-7-(methoxy(oxetan-3-yl)methyl)-2-((4-methoxy-6-methyl-2-oxo-1,2-dihydropyridin-3-yl)methyl)-3,4-dihydroisoquin", Journal of Medicinal Chemistry, vol. 61(3), pp. 650-665 (2018).
International Search Report and Written Opinion of the International Searching Authority for PCT/IB2018/058795, dated Feb. 7, 2019.
Bachmann et al., "EZH2 Expression Is Associated With High Proliferation Rate and Aggressive Tumor Subgroups in Cutaneous Melanoma and Cancers of the Endometrium, Prostate, and Breast." J. Clin. Oncol. (2006), 24:268-273.
Breuer et al., "Increased expression of the EZH2 polycomb group gene in BMI-1-positive neoplastic cells during bronchial carcinogenesis." Neoplasia (2004), 6:736-43.
Crea et al., "Polycomb genes and cancer: Time for clinical application?" Crit. Rev. Oncol. Hematol. (2012), 83:184-193.
Ezponda T, et al., "Molecular pathways: deregulation of histone h3 lysine 27 methylation in cancer-different paths, same destination" Clin Cancer Res. 2014 vol. 1;20(19):5001-8.
Jones PA, et al. "The fundamental role of epigenetic events in cancer" Nat Rev Genet. 2002 vol. 3(6):415-28.
Kleer et al., "EZH2 is a marker of aggressive breast cancer and promotes neoplastic transformation of breast epithelial cells." Proc. Natl. Acad. Sci. USA (2003), 100:11606-11.
Lu et al., "Gene alterations identified by expression profiling in tumor-associated endothelial cells from invasive ovarian carcinoma." Cancer Res. (2007), 67:1757-1768.
Majer et al., "A687V EZH2 is a gain-of-function mutation found in lymphoma patients." FEBS Letters (2012), 586:3448-3451.
Matsukawa et al., "Expression of the enhancer of zeste homolog 2 is correlated with poor prognosis in human gastric cancer." Cancer Sci. (2006), 97:484-491.
McCabe et al., Mutation of A677 in histonemethyltransferase EZH2 in human B-cell lymphonoma promotes hypertrimethylation of histone H3 on lysine 27 (H3K27). Proc Natl. Acad. Sci. USA (2012), 109:2989-2994).
Mimori et al., "Clinical significance of enhancer of zeste homolog 2 expression in colorectal cancer cases." Eur. J. Surg. Oncol. (2005), 31:376-80.
Morin et al., "Somatic mutation of EZH2 (Y641) in Follicular and Diffuse Large B-cell Lymphomas of Germinal Center Origin." Nat. Genetics Feb. 2010; 42(2):181-185.
Ougolkov et al., "Regulation of pancreatic tumor cell proliferation and chemoresistance by the histone methyltransferase enhancer of zeste homologue 2." Clin. Cancer Res. (2008), 14:6790-6796.
Poirier J. T. et al., DNA methylation in small cell lung cancer defines distinct disease subtypes and correlates with high expression of EZH2: Oncogene 2015; 34(48):5869-78.
Sabari J.K. et al. "Unravelling the biology of SCLC: implications for therapy" Nat Rev Clin Oncol. 2017 vol. 14(9):549-561.
Sasaki et al., "The overexpression of polycomb group proteins Bmi1 and EZH2 is associated with the progression and aggressive biological behaviour of hepatocellular carcinoma" Lab. Invest. (2008), 88:873-882.
Semenova E. A. et al., "Origins, genetic landscape, and emerging therapies of small cell lung cancer" Genes Dev. 2015;29(14):1447-62.
Sneeringer et al., "Coordinated activities of wild-type plus mutant EZH2 drive tumor-associated hypertrimethylation of lysine 27 on histone H3 (H3K27) in human B-cell lymphomas", Proc Natl Acad Sci 2010, 107(49):20980-5.

(56) References Cited

OTHER PUBLICATIONS

Sudo et al., "Clinicopathological significance of EZH2 mRNA expression in patients with hepatocellular carcinoma." Br. J. Cancer (2005), 92(9):1754-1758.
Varambally et al., "The polycomb group protein EZH2 is involved in progression of prostate cancer." Nature (2002), 419:624-629.
Wagener et al., "The enhancer of zeste homolog 2 gene contributes to cell proliferation and apoptosis resistance in renal cell carcinoma cells." Int. J. Cancer (2008), 123:1545-1550.
Weikert et al., "Expression levels of the EZH2 polycomb transcriptional repressor correlate with aggressiveness and invasive potential of bladder carcinomas" Int. J Mol. Med. (2005), 16:349-353.

\* cited by examiner

| Group | Dose mg/kg | Schedule | % TGI Day34 | % TGI Day51 | % TGI Day55 | P-value Day51 vs. Vehicle | P-value Day55 vs. Vehicle | N |
|---|---|---|---|---|---|---|---|---|
| Vehicle | - | BID (7/17h) | - | - | - | - | - | 8 |
| Compound 1 | 30 | BID (7/17h) | 50 | 48 | 35 | 0.08 | 0.28 | 9 |
| Compound 1 | 100 | BID (7/17h) | 48 | 58 | 50 | 0.016 | 0.036 | 10 |
| Compound 1 | 300 | BID (7/17h) | 69 | 79 | 72 | 0.0011 | 0.0012 | 10 |

| Group | Dose mg/kg | Schedule | % TGI Day34 | % TGI Day51 | % TGI Day55 | P-value Day51 vs. Vehicle | P-value Day55 vs. Vehicle | N |
|---|---|---|---|---|---|---|---|---|
| Vehicle | - | BID (7/17h) | - | - | - | - | - | 8 |
| Compound 1 | 100 | BID (7/17h) | 48 | 58 | 50 | 0.016 | 0.036 | 10 |
| Cisplatin | 4 | Q7Dx3 | 29 | 61 | 51 | 0.011 | 0.033 | 12 |
| Compound 1 Cisplatin | 100 4 | BID (7/17h) Q7Dx3 | 75 | 95 | 95 | 0.0003 | 0.0006 | 12 |

FIG. 8A
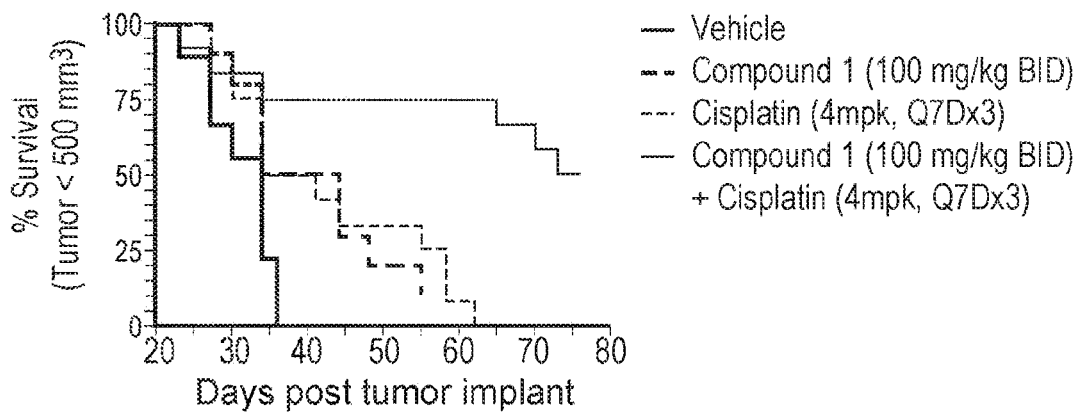
FIG. 8B
| | Vehicle | Cisplatin (Q3Dx3) | Compound 1 (100 mg/kg BID) | Combo | |
|---|---|---|---|---|---|
| Median Survival | 34 | 37.5 | 39 | 74.5 | Days |
| P-value Mantel-Cox | Vehicle | Cisplatin (Q3Dx3) | Compound 1 (100 mg/kg BID) | Combo |
|---|---|---|---|---|
| Vehicle | | 0.073 | 0.055 | 0.0054 |
| Cisplatin (Q3Dx3) | | | 0.069 | 0.0008 |
| Compound 1 (100 mg/kg BID) | | | | 0.0085 |
| Combo | | | | |
FIG. 8C
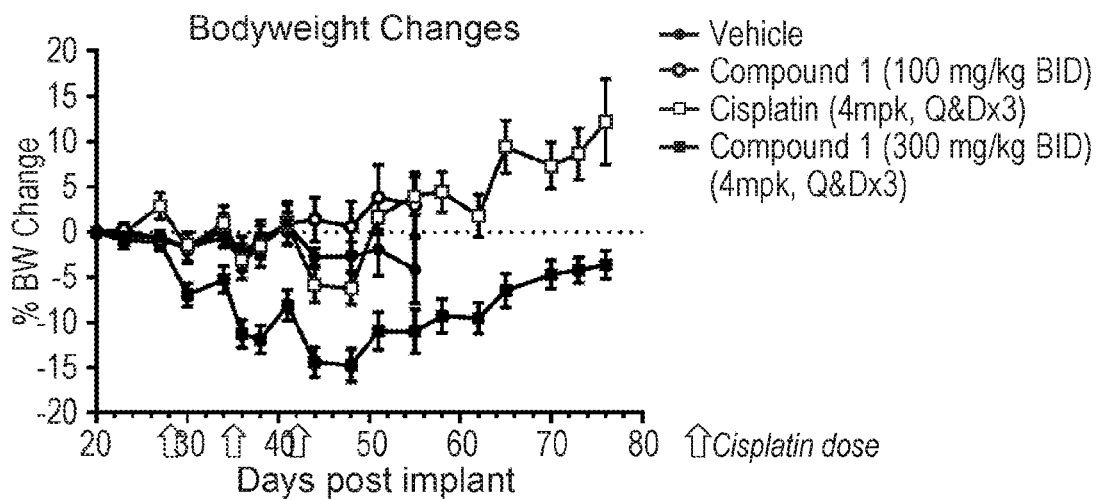

EZH2 INHIBITOR COMBINATION THERAPIES

FIELD OF THE INVENTION

The present invention relates to combination therapies useful for the treatment of cancer. In particular, the invention relates to a combination therapy which comprises an enhancer of zeste homolog 2 (EZH2) inhibitor or a pharmaceutically acceptable salt thereof, with a chemotherapeutic agent or a pharmaceutically acceptable salt thereof. The invention also relates to associated methods of treatment, pharmaceutical compositions, and pharmaceutical uses.

BACKGROUND

Epigenetic alterations play an important role in the regulation of cellular processes, including cell proliferation, cell differentiation and cell survival. The epigenetic silencing of tumor suppressor genes and activation of oncogenes may occur through alteration of DNA methylation patterns, histone modifications, and dysregulation of DNA binding chromatin remodeling complexes. Polycomb genes are a set of epigenetic effectors. EZH2 (enhancer of zeste homolog 2) is the catalytic component of the Polycomb Repressor Complex 2 (PRC2), a conserved multi-subunit complex that represses gene transcription by methylating lysine 27 on Histone H3 (H3K27). EZH2 plays a key role in regulating gene expression patterns that regulate cell fate decisions, such as differentiation and self-renewal. EZH2 is overexpressed in certain cancer cells, where it has been linked to cell proliferation, cell invasion, chemoresistance and metastasis.

High EZH2 expression has been correlated with poor prognosis, high grade, and high stage in several cancer types, including breast, colorectal, endometrial, gastric, liver, kidney, lung, melanoma, ovarian, pancreatic, prostate, and bladder cancers. See Crea et al., *Crit. Rev. Oncol. Hematol.* 2012, 83:184-193, and references cited therein; see also Kleer et al., *Proc. Natl. Acad. Sci. USA* 2003, 100:11606-11; Mimori et al., *Eur. J. Surg. Oncol.* 2005, 31:376-80; Bachmann et al., *J. Clin. Oncol.* 2006, 24:268-273; Matsukawa et al., *Cancer Sci.* 2006, 97:484-491; Sasaki et al. *Lab. Invest.* 2008, 88:873-882; Sudo et al., *Br. J. Cancer* 2005, 92(9):1754-1758; Breuer et al., *Neoplasia* 2004, 6:736-43; Lu et al., *Cancer Res.* 2007, 67:1757-1768; Ougolkov et al., *Clin. Cancer Res.* 2008, 14:6790-6796; Varambally et al., *Nature* 2002, 419:624-629; Wagener et al., *Int. J. Cancer* 2008, 123:1545-1550; and Weikert et al., *Int. J. Mol. Med.* 2005, 16:349-353; Jones P. A. et al., *Nat Rev Genet,* 2002, 3(6):415-428; and Ezponda T. et al., *Clin Cancer Res,* 2014, 20(19):5001-5008.

Recurring somatic mutations in EZH2 have been identified in diffuse large B-cell lymphoma (DLBCL) and follicular lymphomas (FL). Mutations altering EZH2 tyrosine 641 (e.g., Y641C, Y641F, Y641N, Y641S, and Y641H) were reportedly observed in up to 22% of germinal center B-cell DLBCL and 7% of FL. Morin et al., *Nat. Genetics* 2010, 42(2):181-185. Mutations of alanine 677 (A677) and alanine 687 (A687) have also been reported. McCabe et al., *Proc. Natl. Acad. Sci. USA* 2012, 109:2989-2994; Majer et al., *FEBS Letters* 2012, 586:3448-3451. EZH2 activating mutations have been suggested to alter substrate specificity resulting in elevated levels of trimethylated H3K27 (H3K27Me3) (Sneeringer et al., *Proc Natl Acad Sci USA* 2010, 107(49):20980-5).

Small cell lung cancer (SCLC), also known as oat call cancer, constitutes approximately 10-15% of all lung cancers. Small cell carcinoma of the lung usually presents in the central airways and infiltrates the submucosa leading to narrowing of the bronchial airways. Over 70% of patients with small-cell lung carcinoma present with metastatic disease; common sites include liver, adrenals, bone and brain. SCLC is a poorly differentiated neoplasm which can be distinguished by its neuroendocrine (NE) features (Sabari J. K. et al. *Nat Rev Clini Oncol,* 2017, 14(9): 549-561). After diagnosis, SCLC is most commonly classified as either limited state disease (LD) or extensive disease (ED), depending on the absence or presence of distant metastases. Around two-thirds of all SCLC patients are diagnosed with ED. In spite of late detection of SCLC, a good initial response to chemotherapy and radito therapy is observed in the majority of patients. Unfortunately though, following this initial response, almost all patients relapse within 6-12 months with resistant disease (Semenova E. A. et al., *Genes Dev,* 2015, 29(14):1447-1462). Small cell lung cancer is characterised by nearly uniform loss of function of the tumor suppressors TP53 (tumor protein p53) and RB1 (retinoblastoma). Overexpression of EZH2 is observed in all SCLC patients compared to other lung cancer subtypes and normal tissues. Loss of RB1 in SCLC is strongly associated with increased expression of EZH2. EZH2 may therefore have a role in mediating progression of SCLC (Poirier J. T. et al., *Oncogene,* 2015, 34(48): 5869-5878; Gardner E. E. et al., *Cancer Cell,* 2017, 31(2): 286-299).

There remains a need for improved therapies for the treatment of cancers. The combinations of the present invention are believed to have one or more advantages such as greater efficacy than treatment with either therapeutic agent alone; potential to reduce drug interactions; potential to enable an improved dosing schedule; potential to reduce side effects; potential to overcome resistance mechanisms and the like. These, and other advantages of the present invention, are apparent from the description below.

SUMMARY

This invention relates to therapeutic regimens for the treatment of cancer.

This invention relates to a method of treating cancer in a subject comprising administering to the subject a combination therapy which comprises an EZH2 inhibitor, or a pharmaceutically acceptable salt thereof, and a platinum based antineoplastic agent, or a pharmaceutically acceptable salt thereof.

This invention also relates to a combination of an EZH2 inhibitor, or a pharmaceutically acceptable salt thereof, and a platinum based anti-neoplastic agent, or a pharmaceutically acceptable salt thereof.

This invention also relates to a combination of an EZH2 inhibitor, or a pharmaceutically acceptable salt thereof, and a platinum based anti-neoplastic agent, or a pharmaceutically acceptable salt thereof, for use in the treatment of cancer.

This invention also relates to a synergistic combination of an EZH2 inhibitor, or a pharmaceutically acceptable salt thereof, and a platinum based anti-neoplastic agent, or a pharmaceutically acceptable salt thereof.

This invention also relates to a synergistic combination of an EZH2 inhibitor, or a pharmaceutically acceptable salt thereof, and a platinum based anti-neoplastic agent, or a pharmaceutically acceptable salt thereof, for use in the treatment of cancer.

This invention also relates to a pharmaceutical composition comprising an EZH2 inhibitor, or a pharmaceutically acceptable salt thereof, and an platinum based anti-neoplastic agent, or a pharmaceutically acceptable salt thereof, and a pharmaceutically acceptable carrier.

This invention also relates to a kit which comprises a first container, a second container and a package insert, wherein the first container comprises at least one dose of an EZH2 inhibitor, or a pharmaceutically acceptable salt thereof, the second container comprises at least one dose of a platinum based anti-neoplastic agent, or a pharmaceutically acceptable salt thereof, and the package insert comprises instructions for treating a subject for cancer using the medicaments.

In one embodiment of the present invention the subject is a human.

In one embodiment of the present invention the cancer is small cell lung cancer.

In one embodiment of the present invention the cancer is refractory small cell lung cancer.

In one embodiment of the present invention the cancer is relapsed small cell lung cancer.

In one embodiment of the present invention the cancer is small cell lung cancer, which small cell lung cancer is classified as extensive stage disease.

In one embodiment of the present invention the subject is treatment naive.

In one embodiment of the present invention the cancer is relapsed small cell lung cancer and the subject is treatment naive.

In one embodiment of the present invention the cancer is refractory small cell lung cancer and the subject is treatment naive.

In one embodiment of the present invention the cancer is extensive stage disease small cell lung cancer and the subject is treatment naive.

In one embodiment of the present invention the cancer is refractory extensive stage disease small cell lung cancer and the subject is treatment naïve.

In one embodiment of the present invention the cancer is relapsed extensive stage disease small cell lung cancer and the subject is treatment naïve.

In one embodiment of the present invention the EZH2 inhibitor is selected from the group consisting of:
5,8-dichloro-2-[(4-methoxy-6-methyl-2-oxo-1,2-dihydro-pyridin-3-yl)methyl]-7-[methoxy(oxetan-3-yl)methyl]-3,4-dihydroisoquinolin-1(2H)-one;
5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one;
5,8-dichloro-2-[(4-methoxy-6-methyl-2-oxo-1,2-dihydro-pyridin-3-yl)methyl]-7-[(S)-methoxy(oxetan-3-yl)methyl]-3,4-dihydroisoquinolin-1(2H)-one,
5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one;
5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one;
N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide,
N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide;
N-[(4-methoxy-6-methyl-2-oxo-1,2-dihydropyridin-3-yl)methyl]-2-methyl-1-[(1R)-1-[1-(2,2,2-trifluoroethyl)piperidin-4-yl]ethyl]-1H-indole-3-carboxamide;
N-(4,6-dimethyl-2-oxo-1,2-dihydropyridin-3-ylmethyl)-1-isopropyl-3-methyl-6-[6-(4-methylpiperazin-1-yl)pyridin-3-yl]-1H-indole-4-carboxamide,
N-[(6-methyl-2-oxo-4-propyl-1,2-dihydropyridin-3-yl)methyl]-6-[2-(4-methylpiperazin-1-yl)pyridin-4-yl]-1-(propan-2-yl)-1H-indazole-4-carboxamide;
or a pharmaceutically acceptable salt thereof.

In one embodiment of the present invention the EZH2 inhibitor is 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one, or a pharmaceutically acceptable salt thereof.

In one embodiment of the present invention the platinum based anti-neoplastic agent is selected from the group consisting of cisplatin and carboplatin.

In one embodiment of the present invention the platinum based anti-neoplastic agent is cisplatin.

In one embodiment of the present invention the platinum based anti-neoplastic agent is carboplatin.

In one embodiment of the present invention the EZH2 inhibitor is 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one, or a pharmaceutically acceptable salt thereof and the platinum based anti-neoplastic agent is cisplatin.

In one embodiment of the present invention the EZH2 inhibitor is 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one, or a pharmaceutically acceptable salt thereof and the platinum based anti-neoplastic agent is carboplatin.

In one embodiment of the present invention etoposide is further administered.

Each of the embodiments of the present invention described below may be combined with one or more other embodiments of the present invention described herein which is not inconsistent with the embodiment(s) with which it is combined. In addition, each of the embodiments below describing the invention envisions within its scope the pharmaceutically acceptable salts, solvates, hydrates and complexes thereof, and to solvates, hydrates and complexes of salts thereof, including polymorphs, stereoisomers, and isotopically labelled versions thereof of the compounds of the invention. Accordingly, the phrase "or a pharmaceutically acceptable salt thereof" is implicit in the description of all compounds described herein.

BRIEF DESCRIPTION OF THE FIGURES

FIG. 8: Extended Survival of Mice Treated with Cisplatin in Combination with Compound 1 in the EZH2-wt DMS114 Subcutaneous SCLC Xenograft Model. Kaplan Meier survival curve based on a survival cut-off at 500 mm$^3$ tumor burden. Randomization on Day 20 after implant in female NOD/SCID mice. P values are based on a Log-rank test (Mantel-Cox; Graphpad-Prism software). Bodyweight recovery in the two cisplatin treated groups after the 3rd treatment with cisplatin and post Day 55.

DETAILED DESCRIPTION

Figure 1:
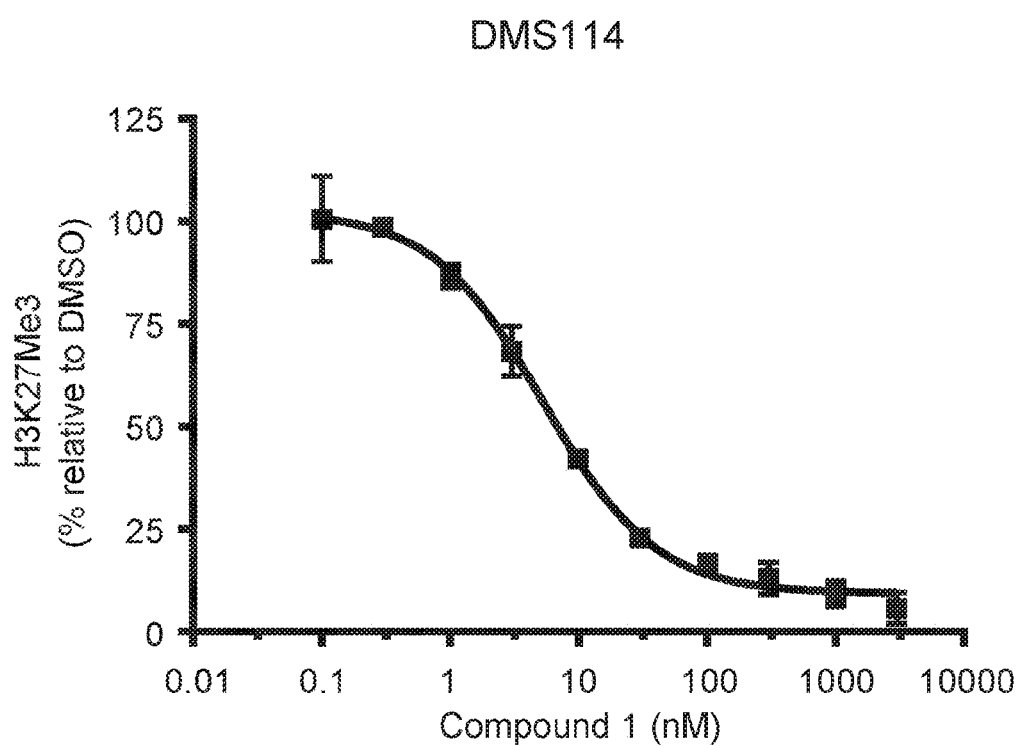
FIG. 1: Inhibition of H3K27Me3 by Compound 1 in DMS114 SCLC Cells. DMS114 SCLC cells were treated with different concentrations of Compound 1 for 3 days and H3K27Me3 levels were assessed using Western Blot analysis. Each data point represents % H3K27Me3 levels at a given compound concentration normalized to DMSO (Mean±SD; n=2 technical replicates). Figure is representative of 5 independent biological replicate experiments.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The term "about" when used to modify a numerically defined parameter (e.g., the dose of a EZH2 inhibitor, the dose of a platinum based anti-neoplastic agent such as cisplatin, the dose of a chemotherapeutic agent such as etoposide, and the like) means that the parameter may vary by as much as 10% above or below the stated numerical value for that parameter. For example a dose of about 5 mg/kg should be understood to mean that the dose may vary between 4.5 mg/kg and 5.5 mg·kg.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

The term "cancer", "cancerous", "malignant" refer to or describe the physiological condition in mammals that is typically characterized by unregulated cell growth. As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. Examples of cancer include, but are not limited to, carcinoma, lymphoma, leukaemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, follicular lymphoma (FL), diffuse large B-cell lymphoma (DLCBCL), acute myeloid leukaemia (AML), multiple myeloma, gastrointestinal (tract) cancer, renal cancer, ovarian cancer, liver cancer, kidney cancer, prostate cancer, castration resistant prostate cancer (CRPC), thyroid cancer, melanoma, chondrosarcoma, neuroblastoma, pancreatic cancer, glioblasoma, multiformer, cervical cancer, brain cancer, stomach cancer, bladder cancer, hepatoma, breast cancer, colon carcinoma, and head and neck cancer.

The term "patient" or "subject" refers to any single subject for which therapy is desired or that is participating in a clinical trial, epidemiological study or used as a control, including humans and mammalian veterinary patients such as cattle, horses, dogs and cats. In certain preferred embodiments, the subject is a human.

The term "treat" or "treating" a cancer as used herein means to administer a combination therapy according to the present invention to a subject having cancer, or diagnosed with cancer, to achieve at least one positive therapeutic effect, such as, for example, reduced number of cancer cells, reduced tumor size, reduced rate of cancer cell infiltration into peripheral organise, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of tumor; remission of the cancer; decreasing symptoms resulting from the cancer; increasing the quality of life of those suffering from the cancer; decreasing the dose of other medications required to treat the cancer; delaying the progression the cancer; curing the cancer; overcoming one o rmore resistance mechanisms of the cancer; and/or prolonging survival of patients the cancer. Positive therapeutic effects in cancer can be measured in a number of ways (see, for example, W. A. Weber, J. Nucl. Med. 50:1S-10S (200)). In some embodiments, the treatment achieved by a combination of the invention is any of the partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow, and includes the amount of time patients have experience a CR or PR, as well as the amount of time patients have experience stable disease (SD). DFS refers to the length of time during and after treatment that the patient remains free of disease. OS refers to a prolongation in life expectancy as compared to naïve or untreated subjects or patients. In some embodiments, response to a combination of the invention is any of PR, CR<PFS, DFS, OR or OS that is assessed using Response Evaluation Criteria in Solid Tumors (RECIST) 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrat-testy and the Wilcon on-test. The term "treatment" also encompasses in vitro and ex vivo treatment, e.g., of a cell, by a reagent, diagnostic, binding compound, or by another cell.

The terms "treatment regimen", "dosing protocol" and "dosing regimen" are used interchangeably to refer to the dose and timing of administration of each therapeutic agent in a combination of the invention.

"Ameliorating" means a lessening or improvement of one or more symptoms as compared to not administering a therapeutic agent of a method or regimen of the invention. "Ameliorating" also includes shortening or reduction in duration of a symptom.

As used herein, an "effective dosage" or "effective amount" of drug, compound or pharmaceutical composition is an amount sufficient to effect any one or more beneficial or desired, including biochemical, histological and/or behavioural symptoms, of the disease, its complications and intermediate pathological phenotypes presenting during development of the disease. For therapeutic use, a "therapeutically effective amount" refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or delaying the progression of the disease of patients. An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Examples of solid tumors are sarcomas, carcinomas, and lymphomas. Leukaemia's (cancers of the blood) generally do not form solid tumors (National Cancer Institute, Dictionary of Cancer Terms).

"Tumor burden" also referred to as a "tumor load", refers to the total amount of tumor material distributed throughout the body. Tumor burden refers to the total number of cancer cells or the total size of tumor(s), throughout the body, including lymph nodes and bone marrow. Tumor burden can be determined by a variety of methods known in the art, such as, e.g., using callipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using callipers, or while in the body using imaging techniques, e.g., bone scan, ultrasound, CR or MRI scans.

The term "additive" is used to mean that the result of the combination of two compounds, components or targeted agents is no greater than the sum of each compound, component or targeted agent individually.

The term "synergy" or "synergistic" are used to mean that the result of the combination of two compounds, components or targeted agents is greater than the sum of each compound, component or targeted agent individually. This improvement in the disease, condition or disorder being treated is a "synergistic" effect. A "synergistic amount" is an amount of the combination of the two compounds, components or targeted agents that results in a synergistic effect, as "synergistic" is defined herein.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

A "non standard clinical dosing regimen" as used herein, refers to a regimen for administering a substance, agent, compound or composition, which is different to the amount, dose or schedule typically used for that substance, agent, compound or composition in a clinical setting. A "non-standard clinical dosing regimen", includes a "non-standard clinical dose" or a "non standard dosing schedule".

A "low dose amount regimen" as used herein refers to a dosing regimen where one or more of the substances, agents, compounds or compositions in the regimen is dosed at a lower amount or dose than typically used in a clinical setting for that agent, for example when that agent is dosed as a singleton therapy.

Enhancer of Zeste Homolog 2

Embodiments of the present invention comprise an EZH2 inhibitor or a pharmaceutically acceptable salt thereof.

As used herein, the term "enhancer of zeste homolog 2 (EZH2) inhibitor" and "EZH2 inhibitor" are used interchangeably and shall be taken to mean an inhibitor of wild type and/or mutant of EZH2. Inhibitors of EZH2 can be determined by methods known to those skilled in the art, for example biological activity can be determined by EZH2 enzymatic assay such as that disclosed in Kung, P. P. et al., *J Med Chem*, 2016, 59, 8306-8325.

Examples of specific EZH2 inhibitors that are useful in the present invention include those disclosed in International patent application PCT/IB2015/054272, which published on 23 Dec. 2015 as WO 2015/193765, the contents of which are included herein by reference. Examples of specific EZH2 inhibitors disclosed therein useful as the EZH2 inhibitor for the present invention include, but are not limited to, EZH2 inhibitors selected from the group consisting of:

5,8-dichloro-2-[(4-methoxy-6-methyl-2-oxo-1,2-dihydropyridin-3-yl)methyl]-7-[methoxy(oxetan-3-yl)methyl]-3,4-dihydroisoquinolin-1(2H)-one, 5,8-dichloro-2-[(4-methoxy-6-methyl-2-oxo-1,2-dihydropyridin-3-yl)methyl]-7-[(R)-methoxy(oxetan-3-yl)methyl]-3,4-dihydroisoquinolin-1(2H)-one;

5,8-dichloro-2-[(4-methoxy-6-methyl-2-oxo-1,2-dihydropyridin-3-yl)methyl]-7-[(S)-methoxy(oxetan-3-yl)methyl]-3,4-dihydroisoquinolin-1(2H)-one;

or a pharmaceutically acceptable salt thereof.

Other examples of specific EZH2 inhibitors that are useful in the present invention include those disclosed in International patent application PCT/IB2013/060682, which published on 26 Jun. 2014 as WO 2014/097041, the contents of which are included herein by reference. Examples of specific EZH2 inhibitors disclosed therein useful as the EZH2 inhibitor for the present invention include, but are not limited to, EZH2 modulators selected from the group consisting of:

5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one, 5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one;

or a pharmaceutically acceptable salt thereof.

Other examples of specific EZH2 inhibitors that are useful in the present invention include those disclosed in International patent application PCT/IB2013/058580, which published on 3 Apr. 2014 as WO 2014/049488, the contents of which are included herein by reference. Examples of specific EZH2 inhibitors disclosed therein useful as the EZH2 inhibitor for the present invention include, but are not limited to, EZH2 inhibitors selected from the group consisting of:

5-[2-(dimethylamino)pyrimidin-5-yl]-N-[(4,6-dimethyl-2-oxo-1,2-dihydropyridin-3-yl)methyl]-2-methyl-3-(1-methyl-1H-pyrazol-5-yl)benzamide;

N-[(4,6-dimethyl-2-oxo-1,2-dihydropyridin-3-yl)methyl]-2-methyl-5-[2-(methylamino)pyrimidin-5-yl]-3-(1-methyl-1H-pyrazol-5-yl)benzamide;

N-[(4,6-dimethyl-2-oxo-1,2-dihydropyridin-3-yl)methyl]-3-(1,4-dimethyl-1H-pyrazol-5-yl)-2-methyl-5-[2-(methylamino)pyrimidin-5-yl]benzamide;

5-(6-aminopyridin-3-yl)-N-[(4,6-dimethyl-2-oxo-1,2-dihydropyridin-3-yl)methyl]-2-methyl-3-(1-methyl-1H-pyrazol-5-yl)benzamide;

N-[(4,6-dimethyl-2-oxo-1,2-dihydropyridin-3-yl)methyl]-3-(1,4-dimethyl-1H-pyrazol-5-yl)-2-methyl-5-(2-morpholin-4-ylpyrimidin-5-yl)benzamide;

N-[(4,6-dimethyl-2-oxo-1,2-dihydropyridin-3-yl)methyl]-3-(1,4-dimethyl-1H-pyrazol-5-yl)-2-methyl-5-{2-[(1S,4S)-2-oxa-5-azabicyclo[2.2.1]hept-5-yl]pyrimidin-5-yl}benzamide;

N-[(4,6-dimethyl-2-oxo-1,2-dihydropyridin-3-yl)methyl]-3-(1,4-dimethyl-1H-pyrazol-5-yl)-2-methyl-5-{2-[3-oxa-8-azabicyclo[3.2.1]oct-8-yl]pyrimidin-5-yl}benzamide;

N-[(4,6-dimethyl-2-oxo-1,2-dihydropyridin-3-yl)methyl]-3-(1,4-dimethyl-1H-pyrazol-5-yl)-5-[2-(3-fluoroazetidin-1-yl)pyrimidin-5-yl]-2-methylbenzamide; and N-[(4,6-dimethyl-2-oxo-1,2-dihydropyridin-3-yl)methyl]-2-methyl-5-[6-(4-methylpiperazin-1-yl)pyridin-3-yl]-3-(1-methyl-1H-pyrazol-5-yl)benzamide;

or a pharmaceutically acceptable salt thereof.

Other examples of specific EZH2 inhibitors that are useful in the present invention include those disclosed in International patent application PCT/US2011/035336, which published on 10 Nov. 2011 as WO 2011/140324, the contents of which are included herein by reference.

Other examples of specific EZH2 inhibitors that are useful in the present invention include those disclosed in International patent application PCT/US2011/035340, which published on 10 Nov. 2011 as WO 2011/140325, the contents of which are included herein by reference.

Other examples of specific EZH2 inhibitors that are useful in the present invention include those disclosed in International patent application PCT/US2011/035344, which published on 12 Jan. 2012 as WO 2012/005805, the contents of which are included herein by reference.

Other examples of specific EZH2 inhibitors that are useful in the present invention include those disclosed in International patent application PCT/US2012/058188, which published on 4 Apr. 2013 as WO 2013/049770, the contents of which are included herein by reference.

Other examples of specific EZH2 inhibitors that are useful in the present invention include those disclosed in International patent application PCT/US2013/041115, which published on 21 Nov. 2013 as WO 2013/173441, the contents of which are included herein by reference.

Other examples of specific EZH2 inhibitors that are useful in the present invention include those disclosed in International patent application PCT/US2011/051258, which published on 15 Mar. 2012 as WO 2012/034132, the contents of which are included herein by reference.

Other examples of specific EZH2 inhibitors that are useful in the present invention include those disclosed in International patent application PCT/US2012/026953, which published on 7 Sep. 2012 as WO 2012/118812, the contents of which are included herein by reference.

Other examples of specific EZH2 inhibitors that are useful in the present invention include those disclosed in International patent application PCT/US2012/033648, which published on 18 Oct. 2012 as WO 2012/142504, the contents of which are included herein by reference. Examples of specific EZH2 inhibitors disclosed therein useful as the EZH2 inhibitor for the present invention include:

N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide;

or a pharmaceutically acceptable salt thereof.

Other examples of specific EZH2 inhibitors that are useful in the present invention include those disclosed in International patent application PCT/US2012/033662, which published on 18 Oct. 2012 as WO 2012/142513, the contents of which are included herein by reference.

Other examples of specific EZH2 inhibitors that are useful in the present invention include those disclosed in International patent application PCT/US2011/061740, which published on 24 May 2012 as WO 2012/068589, the contents of which are included herein by reference.

Other examples of specific EZH2 inhibitors that are useful in the present invention include those disclosed in International patent application PCT/US2013/025639, which published on 15 Aug. 2013 as WO 2013/120104, the contents of which are included herein by reference.

Other examples of specific EZH2 inhibitors that are useful in the present invention include those disclosed in International patent application PCT/US2014/015706, which published on 14 Aug. 2014 as WO 2014/124418, the contents of which are included herein by reference.

Other examples of specific EZH2 inhibitors that are useful in the present invention include those disclosed in International patent application PCT/US2013/065112, which published on 24 Aug. 2014 as WO 2014/062720, the contents of which are included herein by reference.

In one embodiment the EZH2 inhibitor useful for the present invention is:

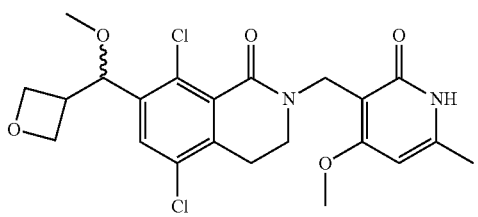

5,8-dichloro-2-[(4-methoxy-6-methyl-2-oxo-1,2-dihydro-pyridin-3-yl)methyl]-7-[methoxy(oxetan-3-yl)methyl]-3,4-dihydroisoquinolin-1(2H)-one;

or a pharmaceutically acceptable salt thereof, which is disclosed in International patent application PCT/IB2015/054272, which published on 23 Dec. 2015 as WO 2015/193765, the contents of which are included herein by reference.

In one embodiment the EZH2 inhibitor useful for the present invention is:

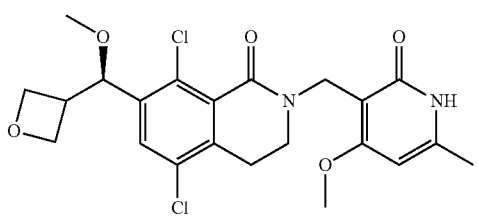 [SMILES: COc1cc(C)[nH]c(=O)c1CN1CCc2c(Cl)cc(C(OC)C3COC3)c(Cl)c2C1=O]

5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one;

or a pharmaceutically acceptable salt thereof which is disclosed in International patent application PCT/IB2015/054272, which published on 23 Dec. 2015 as WO 2015/193765, the contents of which are included herein by reference.

In one embodiment the EZH2 inhibitor useful for the present invention is:

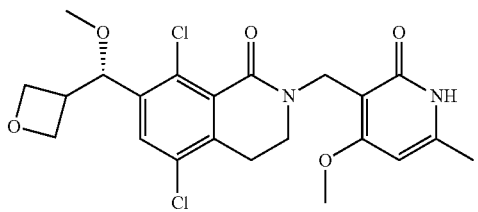 [SMILES: COc1cc(C)[nH]c(=O)c1CN1CCc2c(Cl)cc([C@@H](OC)C3COC3)c(Cl)c2C1=O]

5,8-dichloro-2-[(4-methoxy-6-methyl-2-oxo-1,2-dihydro-pyridin-3-yl)methyl]-7-[(S)-methoxy(oxetan-3-yl)methyl]-3,4-dihydroisoquinolin-1(2H)-one;

or a pharmaceutically acceptable salt thereof which is disclosed in International patent application PCT/IB2015/054272, which published on 23 Dec. 2015 as WO 2015/193765, the contents of which are included herein by reference.

In one embodiment the EZH2 inhibitor useful for the present invention is:

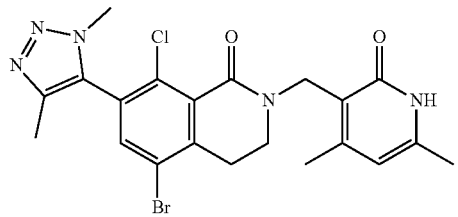 [SMILES: Cc1cc(C)c(CN2CCc3c(Br)cc(-c4c(C)nnn4C)c(Cl)c3C2=O)c(=O)[nH]1]

5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one;

or a pharmaceutically acceptable salt thereof, which is disclosed in International patent application PCT/IB2013/060682, which published on 26 Jun. 2014 as WO 2014/097041, the contents of which are included herein by reference.

In one embodiment the EZH2 inhibitor useful for the present invention is:

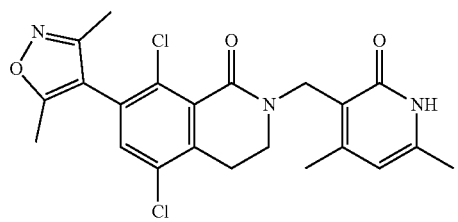 [SMILES: Cc1cc(C)c(CN2CCc3c(Cl)cc(-c4c(C)noc4C)c(Cl)c3C2=O)c(=O)[nH]1]

5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one;

or a pharmaceutically acceptable salt thereof, which is disclosed in International patent application PCT/IB2013/060682, which published on 26 Jun. 2014 as WO 2014/097041, the contents of which are included herein by reference.

In one embodiment the EZH2 inhibitor useful for the present invention is:

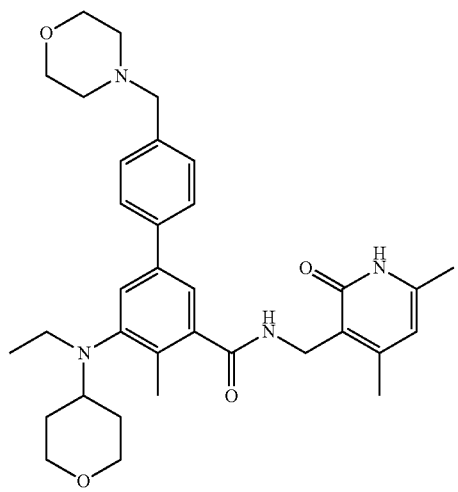 [SMILES: CCN(c1cc(-c2ccc(CN3CCOCC3)cc2)cc(C(=O)NCc2c(C)cc(C)[nH]c2=O)c1C)C1CCOCC1]

N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide or a pharmaceutically acceptable salt thereof, also known as tazemetostat, EPZ-5687 or EPZ-6438 and which is disclosed in International patent application PCT/US2012/033648, which published on 18 Oct. 2012 as WO 2012/142504, the contents of which are included herein by reference.

In one embodiment the EZH2 inhibitor useful for the present invention is:

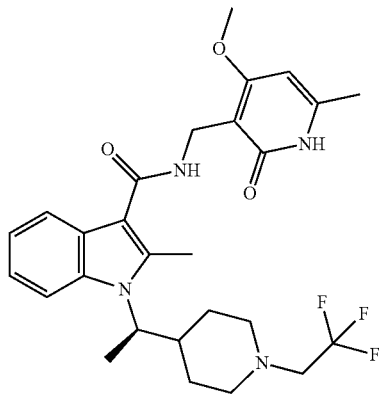 [SMILES: COc1cc(C)[nH]c(=O)c1CNC(=O)c1c(C)n([C@H](C)C2CCN(CC(F)(F)F)CC2)c2ccccc12]

N-[(4-methoxy-6-methyl-2-oxo-1,2-dihydropyridin-3-yl)methyl]-2-methyl-1-[(1R)-1-[1-(2,2,2-trifluoroethyl)piperidin-4-yl]ethyl]-1H-indole-3-carboxamide or a pharmaceutically acceptable salt thereof, also known as CPI-1205, and which is disclosed in International patent application PCT/US2013/025639, which published on 15 Aug. 2013 as WO 2013/120104, the contents of which are included herein by reference.

In one embodiment the EZH2 inhibitor useful for the present invention is:

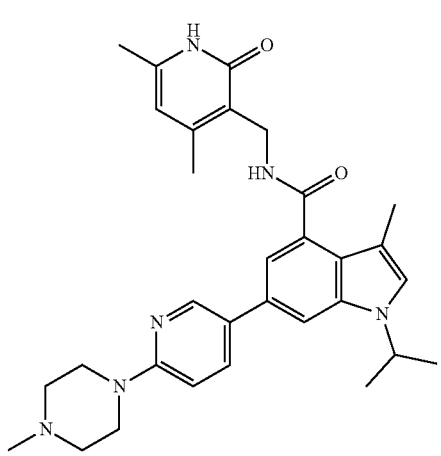 [SMILES: Cc1cc(C)c(CNC(=O)c2cc(-c3ccc(N4CCN(C)CC4)nc3)cc3c2c(C)cn3C(C)C)c(=O)[nH]1]

N-(4,6-dimethyl-2-oxo-1,2-dihydropyridin-3-ylmethyl)-1-isopropyl-3-methyl-6-[6-(4-methylpiperazin-1-yl)pyridin-3-yl]-1H-indole-4-carboxamide or a pharmaceutically acceptable salt thereof, also known as GSK-503, and which is disclosed in International patent application PCT/US2011/035336, which published on 10 Nov. 2011 as WO 2011/140324, the contents of which are included herein by reference.

In one embodiment the EZH2 inhibitor useful for the present invention is:

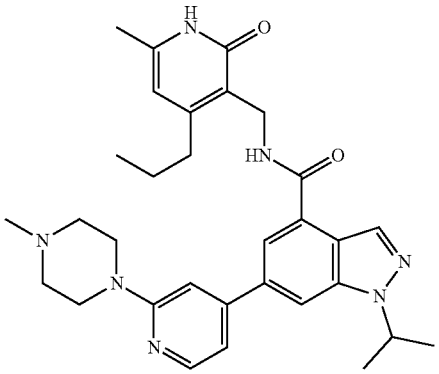 [SMILES: CCCc1cc(C)[nH]c(=O)c1CNC(=O)c1cc(-c2ccnc(N3CCN(C)CC3)c2)cc2c1cnn2C(C)C]

N-[(6-methyl-2-oxo-4-propyl-1,2-dihydropyridin-3-yl)methyl]-6-[2-(4-methylpiperazin-1-yl)pyridin-4-yl]-1-(propan-2-yl)-1H-indazole-4-carboxamide or a pharmaceutically acceptable salt thereof, also known as GSK-126, and which is disclosed in International patent application PCT/US2011/035340, which published on 10 Nov. 2011 as WO 2011/140325, the contents of which are included herein by reference.

In one embodiment the EZH2 inhibitor useful for the present invention is:

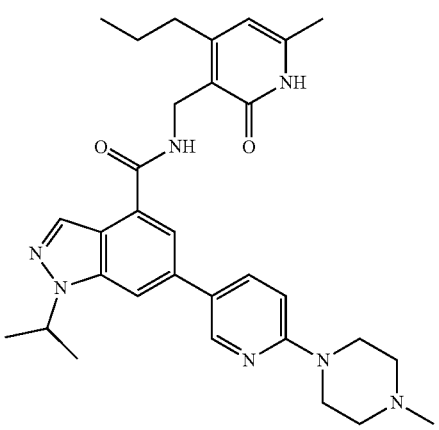 [SMILES: CCCc1cc(C)[nH]c(=O)c1CNC(=O)c1cc(-c2ccc(N3CCN(C)CC3)nc2)cc2c1cnn2C(C)C]

1-isopropyl-N-(6-methyl-2-oxo-4-propyl-1,2-dihydropyridin-3-ylmethyl)-6-[6-(4-methylpiperazin-1-yl)pyridin-3-yl]-1H-indazole-4-carboxamide or a pharmaceutically acceptable salt thereof, which is disclosed in International patent application PCT/US2011/035340, which published on 10 Nov. 2011 as WO 2011/140325, the contents of which are included herein by reference.

In one embodiment the EZH2 inhibitor useful for the present invention is:

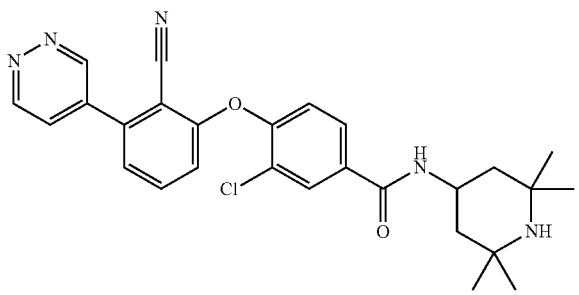 [SMILES: CC1(C)CC(NC(=O)c2ccc(Oc3cccc(-c4ccnnc4)c3C#N)c(Cl)c2)CC(C)(C)N1]

3-chloro-4-[2-cyano-3-(pyridazin-4-yl)phenoxy]-N-(2,2,6,6-tetramethylpiperidin-4-yl)benzamide or a pharmaceutically acceptable salt thereof, which is disclosed in International patent application PCT/US2011/061740, which published on 24 May 2012 as WO 2012/068589, the contents of which are included herein by reference.

In one embodiment the EZH2 inhibitor useful for the present invention is:

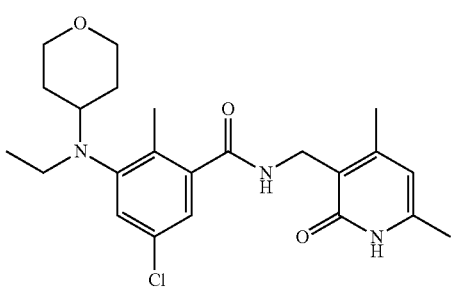 [SMILES: CCN(c1cc(Cl)cc(C(=O)NCc2c(C)cc(C)[nH]c2=O)c1C)C1CCOCC1]

5-chloro-N-[(4,6-dimethyl-2-oxo-1,2-dihydropyridin-3-yl)methyl]-3-[ethyl(tetrahydro-2H-pyran-4-yl)amino]-2-methylbenzamide or a pharmaceutically acceptable salt thereof, which is disclosed in International patent application PCT/US2012/033662, which published on 18 Oct. 2012 as WO 2012/142513, the contents of which are included herein by reference.

In one embodiment the EZH2 inhibitor useful for the present invention is:

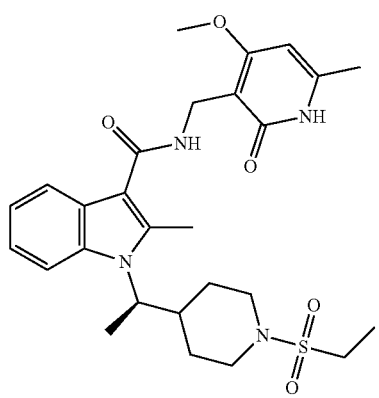 [SMILES: CCS(=O)(=O)N1CCC([C@@H](C)n2c(C)c(C(=O)NCc3c(OC)cc(C)[nH]c3=O)c3ccccc32)CC1]

1-[(1R)-1-[1-(ethylsulfonyl)piperidin-4-yl]ethyl]-N-[(4-methoxy-6-methyl-2-oxo-1,2-dihydropyridin-3-yl)methyl]-2-methyl-1H-indole-3-carboxamide or a pharmaceutically acceptable salt thereof, which is disclosed in International patent application PCT/US2013/025639, which published on 15 Aug. 2013 as WO 2013/120104, the contents of which are included herein by reference.

In one embodiment the EZH2 inhibitor useful for the present invention is:

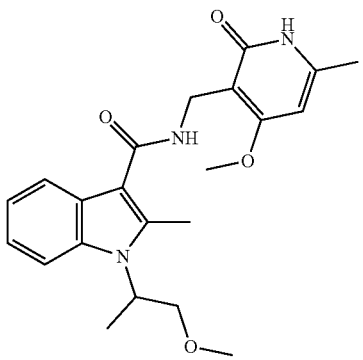 [SMILES: COCC(C)n1c(C)c(C(=O)NCc2c(OC)cc(C)[nH]c2=O)c2ccccc21]

N-[(4-methoxy-6-methyl-2-oxo-1,2-dihydropyridin-3-yl)methyl]-1-(1-methoxypropan-2-yl)-2-methyl-1H-indole-3-carboxamide or a pharmaceutically acceptable salt thereof, which is disclosed in International patent application PCT/US2013/025639, which published on 15 Aug. 2013 as WO 2013/120104, the contents of which are included herein by reference.

In one embodiment the EZH2 inhibitor useful for the present invention is:

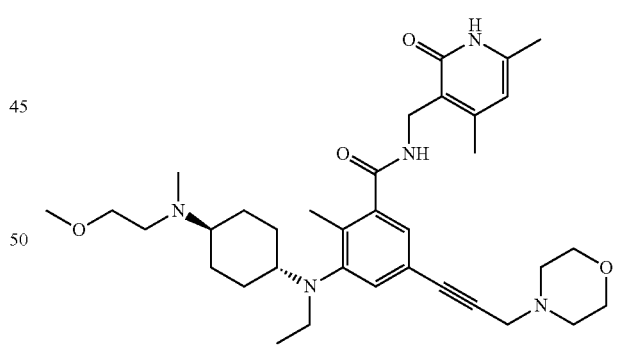

N-[(4,6-dimethyl-2-oxo-1,2-dihydropyridin-3-yl)methyl]-3-(ethyl[trans-4-[(2-methoxyethyl)(methyl)amino]cyclohexyl]amino)-2-methyl-5-[3-(morpholin-4-yl)prop-1-yn-1-yl]benzamide or a pharmaceutically acceptable salt thereof, optionally as the tartrate salt, which compound is disclosed in International patent application PCT/US2013/065112, which published on 24 Apr. 2014 as WO 2014/062720, the contents of which are included herein by reference.

In one embodiment the EZH2 inhibitor useful for the present invention is:

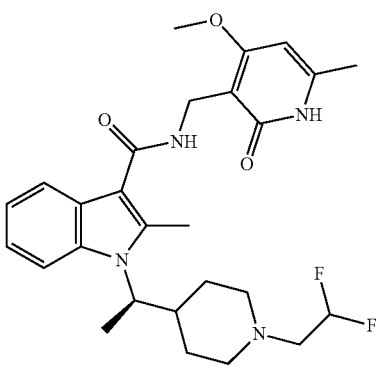 [SMILES: COc1cc(C)[nH]c(=O)c1CNC(=O)c1c(C)n([C@H](C)C2CCN(CC(F)F)CC2)c2ccccc12]

1-[(1R)-1-[1-(2,2-difluoroethyl)piperidin-4-yl]ethyl]-N-[(4-methoxy-6-methyl-2-oxo-1,2-dihydropyridin-3-yl)methyl]-2-methyl-1H-indole-3-carboxamide or a pharmaceutically acceptable salt thereof, which is disclosed in International patent application PCT/US2014/015706, which published on 14 Aug. 2014 as WO 2014/124418, the contents of which are included herein by reference.

In one embodiment the EZH2 inhibitor useful for the present invention is:

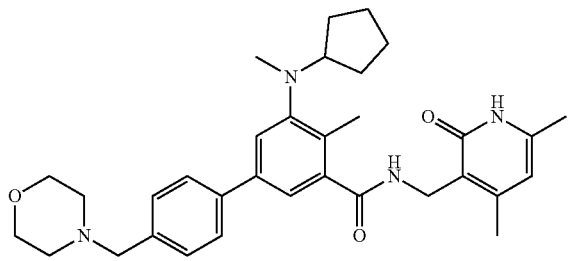 [SMILES: Cc1cc(C)c(CNC(=O)c2cc(-c3ccc(CN4CCOCC4)cc3)cc(N(C)C3CCCC3)c2C)c(=O)[nH]1]

5-[cyclopentyl(methyl)amino]-N-[(4,6-dimethyl-2-oxo-1,2-dihydropyridin-3-yl)methyl]-4-methyl-4'-[(morpholin-4-yl)methyl][1,1'-biphenyl]-3-carboxamide or a pharmaceutically acceptable salt thereof, which is disclosed in International patent application PCT/US2012/033648, which published on 18 Oct. 2012 as WO 2012/142504, the contents of which are included herein by reference.

In one embodiment the EZH2 inhibitor useful for the present invention is:

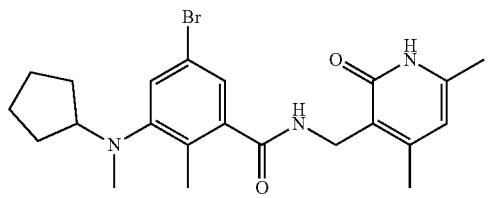 [SMILES: Cc1cc(C)c(CNC(=O)c2cc(Br)cc(N(C)C3CCCC3)c2C)c(=O)[nH]1]

5-bromo-3-[cyclopentyl(methyl)amino]-N-[(4,6-dimethyl-2-oxo-1,2-dihydropyridin-3-yl)methyl]-2-methylbenzamide or a pharmaceutically acceptable salt thereof, which is disclosed in International patent application PCT/US2012/033662, which published on 18 Oct. 2012 as WO 2012/142513, the contents of which are included herein by reference.

In one embodiment the EZH2 inhibitor useful for the present invention is:

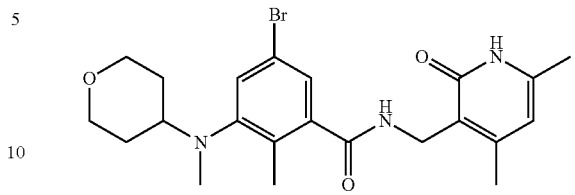

5-bromo-N-[(4,6-dimethyl-2-oxo-1,2-dihydropyridin-3-yl)methyl]-2-methyl-3-[methyl(oxan-4-yl)amino]benzamide or a pharmaceutically acceptable salt thereof, which is disclosed in International patent application PCT/US2012/033662, which published on 18 Oct. 2012 as WO 2012/142513, the contents of which are included herein by reference.

Preferred EZH2 inhibitors useful for the present invention are selected from the group consisting of:

5,8-dichloro-2-[(4-methoxy-6-methyl-2-oxo-1,2-dihydro-pyridin-3-yl)methyl]-7-[methoxy(oxetan-3-yl)methyl]-3,4-dihydroisoquinolin-1(2H)-one;

5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one;

5,8-dichloro-2-[(4-methoxy-6-methyl-2-oxo-1,2-dihydro-pyridin-3-yl)methyl]-7-[(S)-methoxy(oxetan-3-yl)methyl]-3,4-dihydroisoquinolin-1(2H)-one;

5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one, 5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one;

N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide;

N-[(4,6-dimethyl-2-oxo-1,2-dihydropyridin-3-yl)methyl]-5-[ethyl(tetrahydro-2H-pyran-4-yl)amino]-4-methyl-4'-(morpholin-4-ylmethyl)biphenyl-3-carboxamide;

N-[(4-methoxy-6-methyl-2-oxo-1,2-dihydropyridin-3-yl)methyl]-2-methyl-1-[(1R)-1-[1-(2,2,2-trifluoroethyl)piperidin-4-yl]ethyl]-1H-indole-3-carboxamide;

N-(4,6-dimethyl-2-oxo-1,2-dihydropyridin-3-ylmethyl)-1-isopropyl-3-methyl-6[6-(4-methylpiperazin-1-yl)pyridin-3-yl]-1H-indole-4-carboxamide;

N-[(6-methyl-2-oxo-4-propyl-1,2-dihydropyridin-3-yl)methyl]-6-[2-(4-methylpiperazin-1-yl)pyridin-4-yl]-1-(propan-2-yl)-1H-indazole-4-carboxamide;

or a pharmaceutically acceptable salt thereof.

More preferred EZH2 inhibitors useful for the present invention are selected from the group consisting of:

5,8-dichloro-2-[(4-methoxy-6-methyl-2-oxo-1,2-dihydro-pyridin-3-yl)methyl]-7-[methoxy(oxetan-3-yl)methyl]-3,4-dihydroisoquinolin-1(2H)-one;

5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one;

5,8-dichloro-2-[(4-methoxy-6-methyl-2-oxo-1,2-dihydro-pyridin-3-yl)methyl]-7-[(S)-methoxy(oxetan-3-yl)methyl]-3,4-dihydroisoquinolin-1(2H)-one; and 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one,
or a pharmaceutically acceptable salt thereof.

Unless indicated otherwise, all references herein to the EZH2 inhibitors includes references to pharmaceutically acceptable salts, solvates, hydrates and complexes thereof, and to solvates, hydrates and complexes of salts thereof, including polymorphs, stereoisomers, and isotopically labeled versions thereof.

Chemotherapeutic Agents

Embodiments of the present invention relate to chemotherapeutic agents, or pharmaceutically acceptable salts thereof.

In one embodiment the chemotherapeutic agent is a platinum based antineoplastic agent, or a pharmaceutically acceptable salt thereof.

In one embodiment of the present invention, the chemotherapeutic agent is cisplatin.

In one embodiment of the present invention, the chemotherapeutic agent is carboplatin.

In one embodiment of the present invention, the chemotherapeutic agent is etoposide.

In one embodiment of the present invention the chemotherapeutic agent is cisplatin and etoposide.

In one embodiment of the present invention the chemotherapeutic agent is carboplatin and etoposide.

Therapeutic Methods and Uses

The methods and combination therapies of the present inventions are useful for treating cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; (5) inhibiting angiogenesis; or (6) overcoming one or more resistance mechanisms relating to a cancer treatment.

In one embodiment this invention relates to a method of treating cancer in a subject comprising administering to the subject a combination therapy which comprises an EZH2 inhibitor, or a pharmaceutically acceptable salt thereof, and a platinum based antineoplastic agent, or a pharmaceutically acceptable salt thereof.

In one embodiment this invention relates to a method of treating cancer in a subject comprising administering to the subject a combination therapy which consists of an EZH2 inhibitor, or a pharmaceutically acceptable salt thereof, and a platinum based antineoplastic agent, or a pharmaceutically acceptable salt thereof.

In one embodiment this invention relates to a method of treating cancer in a subject comprising administering to the subject a combination therapy which consists essentially of an EZH2 inhibitor, or a pharmaceutically acceptable salt thereof, and a platinum based antineoplastic agent, or a pharmaceutically acceptable salt thereof.

In another aspect, this invention relates to an EZH2 inhibitor, or a pharmaceutically acceptable salt thereof, for use in the treatment of cancer in a subject, wherein the EZH2 inhibitor is used in combination with a platinum based antineoplastic agent, or a pharmaceutically acceptable salt thereof.

In another aspect, this invention relates to a platinum based antineoplastic agent, or a pharmaceutically acceptable salt thereof, for use in the treatment of cancer in a subject, wherein the antineoplastic agent is used in combination with an EZH2 inhibitor, or a pharmaceutically acceptable salt thereof.

In another aspect, this invention relates to a combination of an EZH2 inhibitor, or a pharmaceutically acceptable salt thereof, and a platinum based antineoplastic agent, or a pharmaceutically acceptable salt thereof.

In another aspect, this invention relates to a combination of an EZH2 inhibitor, or a pharmaceutically acceptable salt thereof, and a platinum based antineoplastic agent, or a pharmaceutically acceptable salt thereof, for use as a medicament.

In another aspect, this invention relates to a combination of an EZH2 inhibitor, or a pharmaceutically acceptable salt thereof, and a platinum based antineoplastic agent, or a pharmaceutically acceptable salt thereof, for use in the treatment of cancer in a subject.

In another aspect, this invention relates to a synergistic combination of an EZH2 inhibitor, or a pharmaceutically acceptable salt thereof, a platinum based antineoplastic agent, or a pharmaceutically acceptable salt thereof.

In another aspect, this invention relates to a synergistic combination of an EZH2 inhibitor, or a pharmaceutically acceptable salt thereof, and a platinum based antineoplastic agent, or a pharmaceutically acceptable salt thereof, for use as a medicament.

In another aspect, this invention relates to a synergistic combination of an EZH2 inhibitor, or a pharmaceutically acceptable salt thereof, and a platinum based antineoplastic agent, or a pharmaceutically acceptable salt thereof, for use in the treatment of cancer in a subject.

In another aspect, this invention relates to the use of an EZH2 inhibitor, or a pharmaceutically acceptable salt thereof, and a platinum based antineoplastic agent, or a pharmaceutically acceptable salt thereof, in the manufacture of a medicament for the treatment of cancer in a subject.

In another aspect, this invention relates to a pharmaceutical composition comprising an EZH2 inhibitor, or a pharmaceutically acceptable salt thereof, and a pharmaceutically acceptable carrier for use in the treatment of cancer in a subject, wherein the pharmaceutical composition comprising the EZH2 inhibitor is used in combination with a pharmaceutical composition comprising a platinum based antineoplastic agent, or a pharmaceutically acceptable salt thereof, and a pharmaceutically acceptable carrier.

In another aspect, this invention relates to a pharmaceutical composition comprising a platinum based antineoplastic agent, or a pharmaceutically acceptable salt thereof, and a pharmaceutically acceptable carrier for use in the treatment of cancer in a subject, wherein the pharmaceutical composition comprising the platinum based antineoplastic agent is used in combination with a pharmaceutical composition comprising an EZH2 inhibitor, or a pharmaceutically acceptable salt thereof, and a pharmaceutically acceptable carrier.

In another aspect, this invention relates to a pharmaceutical composition comprising an EZH2 inhibitor, or a pharmaceutically acceptable salt thereof, and a platinum based antineoplastic agent, or a pharmaceutically acceptable salt thereof, and a pharmaceutically acceptable carrier, for use in the treatment of cancer in a subject.

In one embodiment of the invention, the subject is a mammal.

In one embodiment of the invention, the subject is a human.

In some embodiments the methods and combinations of the present invention may be useful for the treatment of cancers including but not limited to cancers of the:
circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

Still more specifically, examples of "cancer" when used herein in connection with the present invention include cancer selected from lung cancer (NSCLC and SCLC), breast cancer (including triple negative breast cancer, hormone positive breast cancer, and HER2 positive breast cancer), ovarian cancer, colon cancer, rectal cancer, cancer of the anal region, prostrate cancer (including hormone sensitive prostate cancer and hormone refractory prostate cancer, also known as castration resistant prostate cancer), hepatocellular carcinoma, diffuse large B-cell lymphoma, follicular lymphoma, melanoma or a combination of one or more of the foregoing cancers.

In one embodiment of the invention, the cancer is a solid tumor.

In one embodiment the cancer is prostate cancer.

In one embodiment the cancer is hormone sensitive prostate cancer.

In one embodiment the cancer is castration resistant prostate cancer, also known as hormone refractory prostate cancer or androgen independent prostate cancer.

In one embodiment the cancer is non-metastatic castration resistant prostate cancer.

In one embodiment the cancer is metastatic castration resistant prostate cancer.

In one embodiment the cancer is breast cancer.

In one embodiment the cancer is triple negative breast cancer.

In one embodiment the cancer is hormone positive breast cancer, including estrogen positive and/or progesterone positive breast cancer.

In one embodiment the cancer is HER2 positive breast cancer.

In one embodiment the cancer is hepatocellular carcinoma.

In one embodiment the cancer is small cell lung cancer.

In one embodiment the cancer is refractory small cell lung cancer.

In one embodiment the cancer is relapsed small cell lung cancer.

In one embodiment the cancer is refractory small cell lung cancer and the subject is treatment naive.

In one embodiment the cancer is relapsed small cell lung cancer and the subject is treatment naive.

In one embodiment the cancer is small cell lung cancer, which small cell lung cancer is classified as limited stage disease.

In one embodiment the cancer is small cell lung cancer, which small cell lung cancer is classified as extensive stage disease.

In one embodiment the cancer is extensive stage disease small cell lung cancer and the subject is treatment naive.

In one embodiment the cancer is refractory extensive stage disease small cell lung cancer and the subject is treatment naive.

In one embodiment the cancer is relapsed extensive stage disease small cell lung cancer and the subject is treatment naive.

In one embodiment the cancer is small cell lung cancer, which small cell lung cancer is characterised by loss of function of the tumor suppressor TP53.

In one embodiment the cancer is small cell lung cancer, which small cell lung cancer is characterised by loss of function of the tumor suppressor RB1.

In one embodiment the cancer is small cell lung cancer, which small cell lung cancer is characterised by loss of function of the tumor suppressor TP53 and loss of function of the tumor suppress RB1.

In one embodiment the cancer is small cell lung cancer, which small cell lung cancer is classified as limited stage disease, and the small cell lung cancer is characterised by loss of function of the tumor suppressor TP53.

In one embodiment the cancer is small cell lung cancer, which small cell lung cancer is classified as limited stage disease, and the small cell lung cancer is characterised by loss of function of the tumor suppressor RB1.

In one embodiment the cancer is small cell lung cancer, which small cell lung cancer is classified as limited stage disease, and the small cell lung cancer is characterised by loss of function of the tumor suppressor TP53 and loss of function of the tumor suppressor RB1.

In one embodiment the cancer is small cell lung cancer, which small cell lung cancer is classified as extensive stage disease, and the small cell lung cancer is characterised by loss of function of the tumor suppressor TP53.

In one embodiment the cancer is small cell lung cancer, which small cell lung cancer is classified as extensive stage disease, and the small cell lung cancer is characterised by loss of function of the tumor suppressor RB1.

In one embodiment the cancer is small cell lung cancer, which small cell lung cancer is classified as extensive stage disease, and the small cell lung cancer is characterised by loss of function of the tumor suppressor TP53 and loss of function of the tumor suppressor RB1.

In one embodiment the cancer is diffuse large B-cell lymphoma.

In one embodiment the cancer is follicular lymphoma.

In one embodiment the cancer is melanoma.

In one embodiment the cancer is locally advanced.

In one embodiment the cancer is non-metastatic.

In one embodiment the cancer is metastatic.

In one embodiment the cancer is refractory.

Inn one embodiment the cancer is relapsed.

In one embodiment the cancer is intolerable of standard treatment.

In another aspect, the invention provides a method of inhibiting cancer cell proliferation in a subject, comprising administering to the subject a combination therapy which comprises an EZH2 inhibitor, or a pharmaceutically acceptable salt thereof, and a platinum based antineoplastic agent, or a pharmaceutically acceptable salt thereof, in an amount effective to inhibit cell proliferation.

In another aspect, the invention provides a method of inhibiting cancer cell invasiveness in a subject, comprising administering to the subject a combination therapy which comprises an EZH2 inhibitor, or a pharmaceutically acceptable salt thereof, and a platinum based antineoplastic agent, or a pharmaceutically acceptable salt thereof, in an amount effective to inhibit cell invasiveness.

In another aspect, the invention provides a method of inhibiting cancer cell metastasis in a subject, comprising administering to the subject a combination therapy which comprises an EZH2 inhibitor, or a pharmaceutically acceptable salt thereof, and a platinum based antineoplastic agent, or a pharmaceutically acceptable salt thereof, in an amount effective to inhibit cell metastasis.

In another aspect, the invention provides a method of inducing apoptosis in cancer cells in a subject, comprising administering to the subject a combination therapy which comprises an EZH2 inhibitor, or a pharmaceutically acceptable salt thereof, and a platinum based antineoplastic agent, or a pharmaceutically acceptable salt thereof, in an amount effective to induce apoptosis.

In a further aspect, the invention provides a method of inducing apoptosis in a subject, comprising administering to the subject a combination therapy which comprises an EZH2 inhibitor, or a pharmaceutically acceptable salt thereof, and a platinum based antineoplastic agent, or a pharmaceutically acceptable salt thereof, or pharmaceutically acceptable salt thereof.

"Contacting" refers to bringing a compound or pharmaceutically acceptable salt used in the invention and a cell (e.g. one expressing EZH2) together in such a manner that the compound may asserts its effect (e.g. affect the activity of EZH2), either directly or indirectly. Contacting may be accomplished in vitro (i.e., in an artificial environment such as, e.g., without limitation, in a test tube or culture medium) or in vivo (i.e., within a living organism such as, without limitation, a mouse, rat or rabbit.)

In some embodiments, the cells are in a cell line, such as a cancer cell line. In other embodiments, the cells are in a tissue or tumor, and the tissue or tumor may be in a subject, including a human.

Dosage Forms and Regimens

Each therapeutic agent of the methods and combination therapies of the present invention may be administered either alone, or in a medicament (also referred to herein as a pharmaceutical composition) which comprises the therapeutic agent and one or more pharmaceutically acceptable carriers, excipients, or diluents, according to pharmaceutical practice.

As used herein, the term "combination therapy" refers to the administration of each therapeutic agent of the combination therapy of the invention, either alone or in a medicament, either sequentially, concurrently or simultaneously.

As used herein, the term "sequential" or "sequentially" refers to the administration of each therapeutic agent of the combination therapy of the invention, either alone or in a medicament, one after the other, wherein each therapeutic agent can be administered in any order. Sequential administration is particularly useful when the therapeutic agents in the combination therapy are in different dosage forms, for example, one agent is a tablet and another agent is a sterile liquid, and/or are administered according to different dosing schedules, for example, one agent is administered daily, and the second agent is administered less frequently such as weekly.

As used herein, the term "concurrently" refers to the administration of each therapeutic agent in the combination therapy of the invention, either alone or in separate medicaments, wherein the second therapeutic agent is administered immediately after the first therapeutic agent, but that the therapeutic agents can be administered in any order. In a preferred embodiment the therapeutic agents are administered concurrently.

As used herein, the term "simultaneous" refers to the administration of each therapeutic agent of the combination therapy of the invention in the same medicament.

In one embodiment of the present invention, the EZH2 inhibitor, or a pharmaceutically acceptable salt thereof, is administered before administration of the platinum based antineoplastic agent, or a pharmaceutically acceptable salt thereof.

In one embodiment of the present invention, the platinum based antineoplastic agent, or a pharmaceutically acceptable salt thereof, is administered before administration of the EZH2 inhibitor, or a pharmaceutically acceptable salt thereof.

In one embodiment of the present invention, the EZH2 inhibitor, or a pharmaceutically acceptable salt thereof, is administered concurrently with the platinum based antineoplastic agent, or a pharmaceutically acceptable salt thereof.

In one embodiment of the present invention, the EZH2 inhibitor, or a pharmaceutically acceptable salt thereof, is administered simultaneously with the platinum based antineoplastic agent, or a pharmaceutically acceptable salt thereof.

As will be understood by those skilled in the art, the combination therapy may be usefully administered to a subject during different stages of their treatment.

In one embodiment of the present invention, the combination therapy is administered to a subject who is previously untreated, i.e. is treatment naïve.

In one embodiment of the present invention, the combination therapy is administered to a subject who has failed to achieve a sustained response after a prior therapy with a biotherapeutic or chemotherapeutic agent, i.e. is treatment experienced.

The combination therapy may be administered prior to of following surgery to remove a tumor and/or may be used prior to, during or after radiation therapy, and/or may be used prior to, during or after chemotherapy.

Administration of compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a therapeutic agent of the combination therapy of the present invention may be administered as a single bolus, as several divided doses administered over time, or the dose may be proportionally reduced or increased as indicated by the exigencies of the therapeutic situation. It may be particularly advantageous to formulate a therapeutic agent in a dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, taking into consideration factors such as the severity of the disorder or condition, the rate of administration, the disposition of the compound and the discretion of the prescribing physician. The dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

In some embodiments, at least one of the therapeutic agents in the combination therapy is administered using the same dosage regimen (dose, frequency and duration of treatment) that is typically employed when the agent is used as a monotherapy for treating the same cancer. In other embodiments, the subject received a lower total amount of at least one of the therapeutic agents in the combination therapy than when the same agent is used as a monotherapy, for example a lower dose of therapeutic agent, a reduced frequency of dosing and/or a shorter duration of dosing.

An effective dosage of an EZH2 inhibitor, or a pharmaceutically acceptable salt thereof, is in the range of from about 0.001 to about 100 mg per kg body weight per day, preferably about 1 to about 35 mg/kg/day, in single or divided doses. For a 70 kg human, this would amount to about 0.01 to about 7 g/day, preferably about 0.02 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

In one embodiment, the EZH2 inhibitor, or a pharmaceutically acceptable salt thereof, is administered at a daily dosage of from about 10 mg to about 7000 mg per day, preferably from about 20 mg to about 2500 mg per day, and more preferably from about 50 mg to about 1000 mg per day. In one embodiment the EZH2 inhibitor, or a pharmaceutically acceptable salt thereof, is administered at a daily dosage of about 500 mg per day.

In a preferred embodiment, the EZH2 inhibitor is 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one, or a pharmaceutically acceptable salt thereof, is administered at a daily dosage of from about 50 mg to about 2000 mg per day, about 50 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, about 850 mg per day, about 900 mg per day, about 950 mg per day, about 1000 mg per day, about 1100 mg per day, about 1200 mg per day, about 1300 mg per day, about 1400 mg per day, or about 1500 mg per day. This dose may optionally be sub-divided into small doses, for example a dosage of 150 mg per day could be dosed as 75 mg dose twice per day.

In one embodiment the chemotherapeutic agent is etoposide, which etoposide is administered intravenously in accordance with the approved label, for example at a dose of from 50 to 100 mg/m$^2$ once a day on days 1 to 5; or from 5 to 100 mg/m2$^2$ once a day on days 1, 3 and 5. In one example etoposide may be administered at a dose from 80 to 120 mg/m$^2$, on days 1, 2 and 3 of each 21-day cycle for 1, 2, 3, 4, 5 or 6 cycles. In one embodiment, the chemotherapeutic agent (e.g. etoposide) is used in combination with a platinum based anti-neoplastic agent (e.g. cispatin or carboplatin).

In one embodiment the platinum based anti-neoplastic agent is cisplatin, which cisplatin is administered intravenously in accordance with the approved label. In one example, cisplatin may be administered at a dose of 60-80 mg/m2$^2$ on day 1 of each 21-day cycle, for 1, 2, 3, 4, 5, or 6 cycles.

In one embodiment the platinum based anti-neoplastic agent is carboplatin, which carboplatin is administered intravenously in accordance with the approved label. In one example, carboplatin may be administered to achieve an initial target AUC of 5 to 6 mg/mL/min on day 1 of each 21-day cycle, for 1, 2, 3, 4, 5 or 6 cycles. In one example, carboplatin may be administered at a dose of 400 mg/m$^2$ on day 1 of each 21-day cycle, for 1, 2, 3, 4, 5, or 6 cycles.

Repetition of the administration or dosing regimens, or adjustment of the administration or dosing regimen may be conducted as necessary to achieve the desired treatment. A "continuous dosing schedule" as used herein is an administration or dosing regimen without dose interruptions, e.g. without days off treatment. Repetition of 21 or 28 day treatment cycles without dose interruptions between the treatment cycles is an example of a continuous dosing schedule. In an embodiment, the compounds of the combination of the present invention can be administered in a continuous dosing schedule.

In one embodiment of the present invention, the EZH2 inhibitor, or a pharmaceutically acceptable salt thereof, and the platinum based antineoplastic agent, or a pharmaceutically acceptable salt thereof, are dosed in amounts which are together effective in treating the cancer.

In one embodiment of the present invention, the EZH2 inhibitor, or a pharmaceutically acceptable salt thereof, and the platinum based antineoplastic agent, or a pharmaceutically acceptable salt thereof, are dosed in amounts which are together are synergistic.

In one embodiment of the present invention, the EZH2 inhibitor, or a pharmaceutically acceptable salt thereof, and the platinum based antineoplastic agent, or a pharmaceutically acceptable salt thereof, are dosed in a non-standard dosing regimen.

In one embodiment of the present invention, the EZH2 inhibitor, or a pharmaceutically acceptable salt thereof, and the platinum based antineoplastic agent, or a pharmaceutically acceptable salt thereof, are dosed in a low dose regimen.

Pharmaceutical Compositions and Routes of Administration

A "pharmaceutical composition" refers to a mixture of one or more of the therapeutic agents described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients.

As used herein, a "pharmaceutically acceptable carrier" refers to a carrier or diluent that does not cause significant irritation to an organism and does not abrogate the biological activity and properties of the active compound or therapeutic agent.

In one embodiment, this invention relates to a pharmaceutical composition comprising an EZH2 inhibitor, or a pharmaceutically acceptable salt thereof, and a platinum based antineoplastic agent, or a pharmaceutically acceptable salt thereof, and a pharmaceutically acceptable carrier.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream, or for rectal administration as a suppository.

Exemplary parenteral administration forms include solutions or suspensions of an active compound in a sterile aqueous solution, for example, aqueous propylene glycol or dextrose solutions. Such dosage forms may be suitably buffered, if desired.

The pharmaceutical composition may be in unit dosage forms suitable for single administration of precise amounts.

Pharmaceutical compositions suitable for the delivery of the therapeutic agents of the combination therapies of the present invention, and methods for their preparation will be readily apparent to those skilled in the art. Such compositions and methods for their preparation may be found, for example, in 'Remington's Pharmaceutical Sciences', 19th Edition (Mack Publishing Company, 1995), the disclosure of which is incorporated herein by reference in its entirety.

Therapeutic agents of the combination therapies of the invention may be administered orally. Oral administration may involve swallowing, so that the therapeutic agent enters the gastrointestinal tract, or buccal or sublingual administration may be employed by which the therapeutic agent enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic agents of the combination therapies of the present invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the therapeutic agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets may contain up to about 80 wt % active agent, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles may be found in Verma et al, *Pharmaceutical Technology On-line*, 25(2), 1-14 (2001). The use of chewing gum to achieve controlled release is described in WO 00/35298. The disclosures of these references are incorporated herein by reference in their entireties.

Parenteral Administration

Therapeutic agents of the combination therapies of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of therapeutic agents used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus therapeutic agents of the combination therapies of the invention may potentially be formulated as a solid, semi-solid, or thixotropic liquid for administration as an implanted depot providing modified release of the active compound. Examples of such formulations include drug-coated stents and PGLA microspheres.

The therapeutic agents of the combination therapies of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Therapeutic agents of the combination therapies of the invention may also potentially be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer may contain a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the compound may be micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the therapeutic agent, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the therapeutic agent per actuation and the actuation volume may vary from 1 µL to 100 µL. A typical formulation includes a therapeutic agent, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the therapeutic agent. The overall daily dose may be administered in a single dose or, more usually, as divided doses throughout the day.

Therapeutic agents of the combination therapies of the invention may potentially be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Therapeutic agents of the combination therapies of the invention may also potentially be administered directly to the eye or ear, typically in the form of drops of a micronized suspension or solution in isotonic, pH-adjusted, sterile saline. Other formulations suitable for ocular and aural administration may include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

In one embodiment, a pharmaceutical composition useful for the combination therapy of the present invention comprises only a single therapeutic agent, for example only one single agent selected from the following: (a) an EZH2 inhibitor, or a pharmaceutically acceptable salt thereof; (b) a platinum based anti-neoplastic agent, or a pharmaceutically acceptable salt thereof; and (c) a chemotherapeutic agent, or a pharmaceutically acceptable salt thereof.

In one embodiment, a pharmaceutical composition useful for the combination therapy of the present invention comprises two or three therapeutic agents, for example two or three agents selected from the following: (a) an EZH2 inhibitor, or a pharmaceutically acceptable salt thereof; (b) a platinum based anti-neoplastic agent, or a pharmaceutically acceptable salt thereof; and (c) a chemotherapeutic agent, or a pharmaceutically acceptable salt thereof.

In one embodiment, a pharmaceutical composition useful for the combination therapy of the present invention comprises both an EZH2 inhibitor, or a pharmaceutically acceptable salt thereof, and a chemotherapeutic agent, or a pharmaceutically acceptable salt thereof.

In one embodiment, a pharmaceutical composition useful for the combination therapy of the present invention comprises both an EZH2 inhibitor, or a pharmaceutically acceptable salt thereof, and a platinum based anti-neoplastic agent, or a pharmaceutically acceptable salt thereof.

Kits

The therapeutic agents of the combination therapies of the present invention may conveniently be combined in the form of a kit suitable for coadministration of the compositions.

In one aspect, the present invention relates to a kit which comprises a first container, a second container and a package insert, wherein the first container comprises at least one dose of an EZH2 inhibitor, or a pharmaceutically acceptable salt thereof, the second container comprises at least one dose of a platinum based anti-neoplastic agent, or a pharmaceutically acceptable salt thereof, and the package insert comprises instructions for treating a subject for cancer using the medicaments.

In one aspect, the present invention relates to a kit which comprises a first container, a second container, a third container, and a package insert, wherein the first container comprises at least one dose of an EZH2 inhibitor, or a pharmaceutically acceptable salt thereof; the second container comprises at least one dose of a platinum based anti-neoplastic agent, or a pharmaceutically acceptable salt thereof; the third container comprises at least one dose of a chemotherapeutic agent, or a pharmaceutically acceptable salt thereof; and the package insert comprises instructions for treating a subject for cancer using the medicaments. In one embodiment, the kit of the present invention may comprise one or more of the active agents in the form of a pharmaceutical composition, which pharmaceutical composition comprises an active agent, or a pharmaceutically acceptable salt thereof, and a pharmaceutically acceptable carrier. The kit may contain means for separately retaining said compositions, such as a container, divided bottle, or divided foil packet. An example of such a kit is the familiar blister pack used for the packaging of tablets, capsules and the like.

The kit may be particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid. The kit may further comprise other materials that may be useful in administering the medicaments, such as diluents, filters, IV bags and lines, needles and syringes, and the like.

Further Therapeutic Agents

In a further aspect, the methods and combination therapies of the present invention may additionally comprise administering a further anti-cancer agents, such as anti-tumor agents, anti-angiogenesis agents, signal transduction inhibitors and antiproliferative agents, which amounts are together effective in treating said cancer. In some such embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, androgen deprivation therapy and anti-androgens. In some embodiments, the anti-tumor agent is selected from antibodies, for example, anti-PD-1 antibodies [e.g. MDX-1106 (nivolumab), MK-3475 (pembrolizumab), CT-011 (pidilizumab), REGN2810 (cemiplimab), BGB-A317 (tislelizumab or BGB-A317), mAb7 (RN888 or PF-06801591), mAb15, AMP-224 (B7-DCIg), AGEN-2034w (aka AGEN-2034), and spartalizumab], anti-PD-L1 antibodies [e.g., YW243.55.S70, MDX-1105 (BMS-936559), MPDL3280A (atezolizumab), MEDI4736 (durvalumab), and MSB0010718C (avelumab)], and anti-CTLA-4 antibodies [e.g. ipilimumab, tremelimumab, and AGEN-1884].

Nivolumab is disclosed in, e.g., PCT Publication No. WO2006/121168 published on 16 Nov. 2006 (International patent application number PCT/JP2006/309606 filed 2 May 2006). Pembrolizumab is disclosed in, e.g., PCT Publication No. WO2009114335 published on 17 Sep. 2009 (International patent application number PCT/US2009/035825 filed 3 Mar. 2009). Pidilizumab is disclosed in, e.g., PCT Publication No. WO2009/101611 published on 20 Aug. 2009 (International patent application number PCT/IL2009/000153 filed 11 Feb. 2009). Cemiplimab is disclosed in, e.g., PCT Publication No. WO2011066389 published on 3 Jun. 2011 (International patent application number: PCT/US2010/058007 filed 24 Nov. 2010). BGB-A317 is disclosed in, e.g., PCT Publication No. WO2015035606 published on 19 Mar. 2015 (International patent application number PCT/CN2013/083467 filed 13 Sep. 2013). mAb7 (RN888 or PF-06801591) is disclosed in, e.g., PCT Publication No. WO2016/092419 published on 16 Jun. 2016 (International patent application number PCT/IB2015/059268 filed 2 Dec. 2015). mAb15 is disclosed in, e.g., PCT Publication No. WO2016/092419 published on 16 Jun. 2016 (International patent application number PCT/IB2015/059268 filed 2 Dec. 2015). AMP-224 (B7-DCIg) is disclosed in, e.g., PCT Publication No. WO2010/027827 published on 11 Mar. 2010 (International patent application number PCT/US2009/054969 filed 25 Aug. 2009) and PCT Publication No. WO2011066342 published on 3 Jun. 2011 (International patent application number PCT/US2010/057940 filed 24 Nov. 2010). AGEN-2034w (aka AGEN-2034) is disclosed in e.g. PCT Publication No. WO2017040790 published on 9 Mar. 2017 (International patent application number PCT/US2016/049913). Spartalizumab is disclosed in, e.g., PCT Publication No. WO/2015112900 published on 30 Jul. 2015 (International patent application number PCT/US2015/012754 filed 23 Jan. 2015).

YW243.55.S70 is disclosed in, e.g., PCT Publication No. WO2010077634 published on 8 Jul. 2010 (International patent application number PCT/US2009/067104 filed 8 Dec. 2009). MDX-1105 (BMS-936559) is disclosed in, e.g., PCT Publication No. WO2018106529 published on 14 Jun. 2018 (International patent application number: PCT/US2017/064207 filed 1 Dec. 2017) and PCT Publication No. WO2007005874 published on 11 Jan. 2007 (International patent application number: PCT/US2006/026046 filed 30 Jun. 2006). MPDL3280A (atezolizumab) is disclosed in, e.g., PCT Publication No. WO2018106529 published on 14 Jun. 2018 (International patent application number: PCT/US2017/064207 filed 1 Dec. 2017). MEDI4736 (durvalumab) is disclosed in, e.g., PCT Publication No. WO2011066389 published on 3 Jun. 2011 (International patent application number: PCT/US2010/058007 filed 24 Nov. 2010) and PCT Publication No. WO2018106529 published on 14 Jun. 2018 (International patent application number: PCT/US2017/064207 filed 1 Dec. 2017). MSB0010718C (avelumab) is disclosed in, e.g., PCT Publication No. WO13079174 published on 6 Jun. 2013 (International patent application number PCT/EP2012/004822 filed 21 Nov. 2012). Ipilimumab is disclosed, e.g., as antibody 10D1 in PCT Publication No. WO01/14424 published on 1 Mar. 2001 (International Patent Application No. PCT/US00/23356 filed 24 Aug. 2000) and also in U.S. Patent Application Publication No. 20150283234 published on 8 Oct. 2015 (U.S. patent application Ser. No. 14/437,029 filed 20 Apr. 2015). Tremelimumab is disclosed as antibody 11.2.1 in U.S. Pat. No. 6,682,736 granted on 27 Jan. 2004 (U.S. patent application Ser. No. 09/472,087 filed 23 Dec. 1999). AGEN-1884 is disclosed, e.g. as Example 1 in PCT Publication No. WO2016196237 published on 8 Dec. 2016 (International Patent Application No. PCT/US2016/034508 filed 27 May 2016).

In one embodiment of the methods and combination therapies of the present invention, the regimen includes a further active agent, wherein the further active agent is etoposide.

These and other aspects of the invention, including the exemplary specific embodiments listed below, will be apparent from the teachings contained herein.

EXAMPLES

Compound 1 was 5,8-dichloro-2-[(4-methoxy-6-methyl-2-oxo-1,2-dihydro-pyridin-3-yl)methyl]-7-[(R)-methoxy (oxetan-3-yl)methyl]-3,4-dihydroisoquinolin-1(2H)-one, disclosed in International patent application PCT/IB2015/054272, which published on 23 Dec. 2015 as WO 2015/193765.

Compound 2 was 5,8-dichloro-7-(3,5-dimethyl-1,2-oxazol-4-yl)-2-[(4,6-dimethyl-2-oxo-1,2-dihydropyridin-3-yl) methyl]-3,4-dihydroisoquinolin-1(2H)-one, disclosed in patent application PCT/IB2013/060682, which published on 26 Jun. 2014 as WO 2014/097041.

Unless otherwise specified, Compound 1 and Compound 2 were prepared as stock solutions in DMSO for further dilution as required.

The following abbreviations are used herein:
ANCOVA—Analysis of covariance
BID—Twice daily
BW—Body weight
BWL—Body weight loss
CR—complete response
DMSO—Dimethylsulfoxide
IP—intraperitoneal N or n—Number of subjects
NOD/SCID—nonobese diabetic/severe combination immunodeficiency
NS—not significant
NSG—NOD scid gamma
PCR—polymerase chain reaction
PO—by mouth
QD—Once Daily
qRT—quantitative real time
RT—reverse transcription
SD—standard deviation
SEM—Standard error of the mean
TGI—Tumor growth inhibition
WT—wild type.
Methods and Protocols for Examples 1 to 9
Cell Culture:

SCLC cell line DMS114 was obtained from American Type Culture Collection (American Type Culture Collection, ATCC CRL-2066) and cultured in Waymouth's Medium MB 752/1 (Gibco/Life Technologies Cat. 11220-035), plus 10% Fetal Bovine Serum (FBS) (Gibco/Life Technologies Cat. 10082-147) and 1% Pen/Strep. COR-L88 (92031917) cells were purchased from ECACC. H841 (CRL-5845), H446 (HTB-171), NCI-H889 (CRL-5817), DMS79 (CRL2049) and H69 (HTB-119) were purchased from American Type Culture Collection and cultured in the recommended media (H841: HITES medium supplemented with 5% FBS; H446, COR-L88, NCI-H889, DMS79 and H69: RPMI-1640 Medium+10% FBS). RPMI1640 was purchased from Invitrogen (Cat. No. 11875-093; Lot. No. 1694256). HITES medium was prepared according to American Type Culture Collection instructions with the base medium of DMEM:F12 Medium (Invitrogen, Cat. No. 11320-033; Lot. No. 1677218) supplemented with a mixture of the following components: 0.005 mg/ml Insulin and 0.01 mg/ml Transferrin, 30 nM Sodium selenite (ITS-X (Invitrogen, Cat. No. 51500-056, Lot. No. 1582940), 10 nM Hydrocortisone (Sigma, Cat. No. H0888-1G, Lot. No. 061M1142V), 10 nM beta-estradiol (Sigma, Cat. No. E2257-1 mg, Lot. No. 107K8630), extra 2 mM L-glutamine for final conc. of 4.5 mM (Invitrogen, Cat. No. 25030-081, Lot. No. 1552995), 5% fetal bovine serum (Invitrogen, Cat. No. 10099-141, Lot. No. 1565565). All cells were maintained in a humidified incubator at 37° C. with 5% carbon dioxide ($CO_2$).

In Cell Western Blot Protocol:

Cells were plated at 1500 cells per well in 96-well black, flat, clear-bottom plates (Falcon, BD-353219). The following day, compounds were added to the wells at 3-fold dilution with a final concentration range from 3 µM to 0.1 nM, leaving some cells empty for controls: "DMSO only (1st and 2nd antibody)" and "DMSO only (2nd antibody only)". After 72 hours, the media was removed and 3.7% of formaldehyde was added in Phosphate-Buffered Saline (PBS, Gibco Life Technologies, Cat. 10010-023) for 20 minutes in a fume hood to fix. Formaldehyde was then removed and 150 µl of ice-cold methanol (MeOH) was added to permeabilize the cells. Plates were wrapped and frozen overnight. The next day, MeOH was removed, Odyssey blocking buffer (150 µl) was added, and plates were kept on a rotating shaker (VWR) for two hours. Blocking buffer was removed and H3K27Me3 antibody (Cell Signaling 9733), which had previously been diluted 1:800 in 50 µl of Odyssey blocking buffer (LiCor #927-40000), was added. Plates were then placed on a rotating shaker (VWR) in a cold room and incubated overnight at 4° C. The next day, the primary antibody was removed, the cells were washed with 1×PBS+0.1% Tween 20 (PBST) a total of 5 times for 5 minutes each. The secondary antibody (Cell Signaling 5151 anti-rabbit) was diluted 1:800 in Odyssey buffer (50 µl) and then added to each well along with DRAQ5 reagent (Cell Signalling #4084) was diluted 1:10,000 in Odyssey buffer (5 mM) for normalization. After 2 hours, the secondary antibody was removed, the plates were washed again 5 times in PBST for 5 minutes each and then fluorescent signal was detected on an Odyssey LiCoR instrument (focus length 3 mm; using both 800 nm (for secondary) and 700 nm filters together (for DRAQ5). $IC_{50}$ values were calculated using a four-parameter fit with GraphPad Prism version 7.02 and arithmetic mean of all biological replicates was calculated.

Cell Growth Inhibition Assay for DMS114 SCLC Cells:

DMS114 SCLC cells were plated in complete cell culture medium described above (1 mL/well) in a 12-well clear, flat bottom polystyrene tissue culture plate (Falcon, Cat. 353225) at a density of 10,000 cells/well. Plates were incubated overnight for 16 hours at 37° C. and 5% $CO_2$. Cells were then treated for 3 days with a 10-point, 3-fold serial dilution of Compound 1 starting at a high concentration of 3 µM. After 3 days, cells from each individual dose treatment were dissociated with Trypsin-EDTA (0.25%) (Gibco/Life Technologies Cat. 25200-056), resuspended in fresh medium, and counted using Vi-Cell cell counter and cell viability analyzer (Beckman Coulter, cat. 383556). Cells from each individual dose treatment were then re-plated in complete cell culture medium as described above (100 μL/well) in a 96-well Ultra Low Attachment (ULA) plate (Corning Inc, Cat. 7007) at a density of 500 cells/well. Cells were again incubated overnight for 16 hours at 37° C. and 5% $CO_2$. The following day, Compound 1 was added with their respective doses as set out above using a 10-point, 3-fold serial dilution of Compound 1 starting at a high concentration of 3 μM. Plates were then incubated at 37° C. and 5% $CO_2$ for additional 14-18 days, with fresh growth medium and drug replenished according to the dosing schedule described above every 3 days. Cells were treated with compound for a total of 17-21 days. At the end of the incubation period, 19 μL of AlamarBlue (ThermoFisher Cat. DAL102) was added to each well and plates were incubated at 37° C. for 16 hours. Plates were then read in an Infinite M200 Pro microplate reader (Tecan Cat. 396235) using a fluorescence excitation wavelength of 540 nm to 570 nm (peak excitation is 570 nm) and emission at 580 nm to 610 nm (peak emission is 585 nm). $IC_{50}$ values were calculated using nonlinear regression dose response curve fit in GraphPad Prism version 7.02.

Cell Growth Inhibition Assay for H841, H446 and H69 SCLC Cells:

H841, H446 and H69 cells were plated in their recommended complete culture medium described above (1 mL/well) in triplicate 12 well plates for each cell line at a density of 100,000 cells per well. Plates were incubated overnight at 37° C. and 5% $CO_2$. Compound 1 stock was prepared at 50 mM in DMSO and was dispensed to several single-use aliquots and stored at −20° C. To prepare the compound plate, Compound 1 was diluted to 3 mM in DMSO and then 3-fold serial dilution were made in DMSO (10 doses in total). 24 hours after cell plating 1 μl of the drug dilutions along with DMSO control was added to the appropriate wells of the 12 well plate containing cells in 1 ml of media (1000× dilution). The final concentration of drug after all dilutions in each well was 3, 1, 0.333, 0.111, 0.037, 0.012, 0.004, 0.001, 0.0005, 0.0002 μM. DMSO was added to 3 replicate control wells. Plates were shaken by hand to properly mix the drug. Cells were then maintained in the incubator at 37° C. After 3 or 4 days, cells were split 1:2 or 1:3 depending on cell growth rate. For suspension cells, cells were mixed thoroughly using a 1 ml pipette and then 500 μl (1:2 split) or 667 μl (1:3 split) of cells was removed. For adherent cells, cells were trypsinized and split 1:2 or 1:3. The same volume of fresh media was added to each well to make the volume up to 1 ml. If the cells were semi-adherent, the suspension cells in the supernatant were collected along with the trypsinized adherent cells. Fresh drug was added to each well as described earlier. Cells were split and media/drug replenishment was repeated similarly every 3-4 days till Day 21. On Day 21, cell morphology was observed under microscope and any morphology changes upon compound treatment were recorded. For suspension cells, cells were then mixed repeatedly by pipetting, aspirated from the triplicate wells and transferred to a 15 mL tube. For adherent cells, supernatant was removed and 500 μl of trypsin was added to each well. After the cells had dissociated from the bottom 1 ml of complete media was added to each well. Cells were broken to single cell suspension, transferred to a 15 mL tube and centrifuged at 1000 rpm for 5 min. Supernatant was removed and cells were re-suspended from the triplicate wells in 1000-3000 μl of media based on the size of the pellets. 50-100 μl of the volume was transferred from the cells+media wells to a 96-well flat bottom black CTG plate (Corning, Cat.CLS3904) and equal volume of CTG reagent was added (from Promega, Cat.G7571, Lot. No. 0000089186). The volume of the cell suspension was adjusted to ensure that the signal was in linear range for the CTG assay (cells are not too many and not too few). The cells were then shaken in dark for 5 min. Cell viability was measured using according to manufacturer's instructions.

To assess the synergistic anti-proliferative effects of combining EZH2 inhibitors with standard of care chemotherapy agents (cisplatin and etoposide, which can be used singly or in combination as standard of care in chemotherapies), each of the cell lines described above were pre-treated with defined doses of Compound 1 in culture flasks for 9 days followed by co-treatment with cisplatin or etoposide in 96-well plates for 4 days. The effects on cell proliferation were assessed using the CellTiter-Glo cell proliferation assay in accordance with the methods described herein, and Chalice Bioinformatics software (Horizon Discovery, version 1.6) was used to analyze the results and calculate the synergy scores. Data is normalized to untreated DMSO/DMSO sample and represented as % of untreated sample. The data was analyzed using Loewe additivity combination model and excess attribute was used to evaluate the magnitude of the observed data that exceeds the additive effect predicted for each dose by the Loewe model.

SLFN11 Western Blotting Protocol:

SCLC cell lines were treated with 500 nM of Compound 1 in DMSO for 7 days and changes in SLFN11 protein levels were then assessed using western blotting. After drug treatment, cells were trypsized (adherent cells), harvested by centrifugation at 2000 rpm at room temperature, washed with PBS, followed by collection of cell pellets by centrifugation. Cell pellets were re-suspended in appropriate volume of RIPA buffer (Sigma; Catalogue #R0278; 100 ul per 5-10×105 cells), incubated on ice for 10-15 min, centrifuged at 12,000 g and 4° C. for 10 min and then supernatant was collected. 15 ug of total protein lysates was run on 4-12% NuPAGE™ Bis-Tris protein gel (NP0336Box) in 1×NuPAGE™ MOPS SDS Running Buffer (NP0001). Gels were run on ice at 80V for 20 minutes and then 150V for 60 minutes. For protein transfer, iBlot2 Dry Blotting system (Cat #: 1621001) was used along with iBlot2 Regular Nitrocellulose Transfer Stacks (Cat #: IB23001) according to manufacturer's instructions. iBlot2 Regular nitrocellulose transfer stacks were assembled and placed into the iBlot2 Dry Blotting system. The transfer was run using the template method P3 according to the manufacture's instructions at a constant voltage of 20V for 7 minutes. After transfer had finished, the nitrocellulose membrane was blocked in 5% non-fat milk for 1 hour at RT with shaking. Primary antibody solution was prepared with SLFN11 antibody (E-4) (Catalog #: sc374339) in 5% non-fat milk blocking buffer at a 1:100 dilution. The membrane was incubated overnight at 4° C. with shaking. The next day, the membrane was washed three times with 1× Tris buffered saline, 0.1% Tween −20 (TBS-T) prepared in house for 10 minutes each on shaker. The membrane was incubated in secondary anti-mouse IgG HRP-linked Ab (Cat #:CST7076S), at a dilution of 1:2,000 in 5% non-fat milk blocking buffer for 1 hour and then washed three times with 1×TBST for 10 minutes on shaker. The signal was detected using the ECL system (Thermo-34078 and -34096) and imaged on the ImageQuant LAS400 imager.

COMET Assay:

The suspension or adherent SCLC cell lines were seeded at a density of 50000 cells/mL in T75 flask and cultured in complete cell culture medium containing Compound 1 at 0.3 μM final concentration in DMSO or DMSO control (0.01%) for 7 days at 37° C. and 5% $CO_2$. Fresh growth medium and drug was replenished every 3-4 days. After 7 days of treatment, cells were treated with 0.3 µM Compound 1 or DMSO control in combination with different doses of cisplatin (Sigma-Alderich Cat #P4394) for 3 days. The cells were harvested by centrifugation and the cell pellets were re-suspended in single cell suspensions at $1\times10^5$ cells/mL in ice cold 1×PBS ($Ca^{++}$ and $Mg^{++}$ free) and stored at room temperature for use. LM Agarose (Trevigen 4250-050-02) was melted in a beaker of boiling water for 5 minutes and the agarose bottle was then placed in a 37° C. incubator to cool. The cells at $1\times10^5$/mL combined with LM Agarose (at 37° C.) at a ratio of 1:10 (v/v) were immediately pipetted (50 µl) onto CometSlide™ (TREVIGEN 4250-050-03) ensuring complete coverage of the sample area. The slides were placed flat at 4° C. in the dark for 10-20 minutes and immersed in a cold Lysis Solution (Trevigen 4250-050-01) and incubated overnight at 4° C. After incubation in the Lysis Solution, the slides were drained and immersed in a freshly prepared Alkaline Unwinding Solution (20 mM NaOH, 1 mM EDTA pH>13) for 1 hour at 4° C. in the dark. The slides were subjected to electrophoresis in TREVIGEN CometAssay ES system (Trevigen 4250-050-ES) with fresh prepared alkaline electrophoresis solution (20 mM NaOH, 1 mM EDTA pH>13) at 21V for 30 minutes. After the electrophoresis the slides were drained in an excess electrophoresis solution and gently immersed twice in $H_2O$ for 5 minutes each followed by 70% ethanol for 5 minutes. The slides were air dried in the dark overnight and stored at room temperature. Dried slides were stained with 100 µl of diluted SYBR Gold (Invitrogen Cat #S11494 1:10000 in TE buffer) for a few minutes in the dark. The stained slides were imaged by Nikon fluorescence microscopy (maximum excitation/emission at 496 nm/522 nm).

γ-H2AX Staining: The sterile SLIP-RITE cover glasses (ThermoScience 22×22#1.5 Cat#152222) were placed onto 6-well plates. $6\times10^4$ cells were seeded onto each cover glass and cultured in 2 ml of complete culture mediums containing 0.3 µM Compound 1 in DMSO or DMSO control (0.01%) at 37° C. and 5% $CO_2$, with fresh growth medium and drug replenished every 3-4 days for 7 days. After 7 days of treatment, cells were treated with 0.3 µM Compound 1 in DMSO or DMSO control in combination with different doses of cisplatin (Sigma-Alderich Cat # P4394) overnight (16 hr). At the end of combination treatment, the cells were washed 3 times with 1× Phosphate buffered saline (PBS) ($Ca^{++}$ and $Mg^{++}$ free), fixed in 1 ml of 4% paraformaldehyde (Electron Microscopy Sciences Cat #15710), and stored overnight at 4° C. After fixation the cells were washed 3 times in 1×PBS and permeabilized by incubation in 1 ml of PBS containing 0.25% Triton X-100 (Sigma, Catalogue # T8787) at room temperature for 10 minutes. After permeabilization the cells were washed 3 times with 1×PBS and incubated with 10% donkey serum (Sigma-Aldrich Cat # D9663, 1:10 diluted in PBS) at room temperature for 1 hour to block unspecific binding of antibodies. After blocking, the cells were incubated with mouse anti-phospho-Histone H2A.X (Ser139) antibody (Millipore Cat #05-636, 1:1000 diluted in 1% BSA) overnight at 4° C. The following day the cells were washed 3 times in 1×PBS and incubated with Alexa Fluor™ 488 donkey anti-mouse IgG antibody (Invitrogen Cat # A21202, 1:2000 diluted into 1% BSA) for 1 hour at room temperature. Cell were then washed 3 times with 1×PBS before mounting. The cover glasses with cells were placed and mounted by Fluoromount-G™ with DAPI (Invitrogen Cat #004959-52) onto a COLORFROST PLUS microscope slide (ThermoSciences Ca #9991004). The mounted slides were imaged on Nikon A1R Confocal microscopy.

EZH2-WT DMS114 SCLC In Vivo Xenograft Studies:

(i) Compound Formulation: Compound 1 was formulated as a wet-milled nanosuspension (24 hr milling in 2.5% w/v polyvinyl pyrrolidone (PVP), 0.5% w/v Macrogol 15 Hydroxystearate (Kolliphor HS15) aqueous, with <1 µm particle-size distribution (PSD; ~650 nm median diameter (d50)) for oral gavage administration.

(ii) Cell Implant, Compound Dosing and Tissue Collection: Immune deficient female mice with a severe combined immunodeficiency (SCID) mutation in a non-obese diabetic background (NOD SCID; 6 to 8 week old; NOD.CB17-Prkdcscid/NCrCrl from Charles River Laboratories) received a subcutaneous (SC) implant of $7.5\times10^6$ DMS114 cells (in 1:1 matrigel (Trevigen, Cultrex BME Path Clear®, Lot #: 30625F14), total volume 200 µl) into the right flank. Tumor volume and body weight were measured twice a week. On Day 20 post implant, 64 mice were randomized, based on tumor size at a geometric mean (geomean) of about 160 $mm^3$, into 6 groups corresponding to dose (Table 1). Compounds were administered at 10 ml/kg by oral gavage (Compound 1; BID (7/17 hours apart)) or intraperitoneal injection (cisplatin), respectively. The cisplatin dosing schedule was once a week for 3 weeks (Q7Dx3) and started 7 days after the randomization and treatment initiation with Compound 1.

TABLE 1

Definition of Study Arms, Cisplatin and Compound 1 Doses, Dosing Regimens, and Routes

| Group # | Drug | n | Dose (mg/kg/dose) | Daily Dose (mg/kg/day) | Formulation | Dosing Route | Regimen |
|---|---|---|---|---|---|---|---|
| 1 | Vehicle | 8 (10)$^a$ | 0 | 0 | wet-milled nanosuspension | PO | BID (7/17 hours apart) |
| 2 | Compound 1 | 9 (10)$^a$ | 30 | 60 | wet-milled nanosuspension | PO | BID (7/17 hours apart) |
| 3 | Compound 1 | 10 | 100 | 200 | wet-milled nanosuspension | PO | BID (7/17 hours apart) |
| 4 | Compound 1 | 10 | 300 | 600 | wet-milled nanosuspension | PO | BID (7/17 hours apart) |
| 5 | Cisplatin | 12 | 4 | 4 | Saline | IP | Q7D x3 |

TABLE 1-continued

Definition of Study Arms, Cisplatin and Compound 1 Doses, Dosing Regimens, and Routes

| Group # | Drug | n | Dose (mg/kg/dose) | Daily Dose (mg/kg/day) | Formulation | Dosing Route | Regimen |
|---|---|---|---|---|---|---|---|
| 6 | Cisplatin | 12 | 4 | 4 | Saline | IP | Q7D x3 BID |
|   | Compound 1 |   | 100 | 200 | wet-milled nanosuspension | PO | (7/17 hours) |

BID = Twice daily; IP = Intraperitoneal; n = sample number; PO = By mouth; Q7D x 3 = Once a week for 3 weeks.
[a]Number of mice in the group at study start. Some animals in the vehicle group (n = 2) and in the Compound 1 30 mg/kg group (n = 1) were sacrificed prior to the end of the study. Therefore, data from these animals were excluded from the TGI and statistical analysis as well as the 55 day plots shown below.

On Day 55, study groups 1, 2, 3 and 4 were terminated (Table 1). Tumor (snap frozen) samples were collected at 4 hours post last dose for pharmacodynamic (PD) analysis. Both cisplatin treated groups (5 and 6) were kept on study until Day 81 post randomization to monitor tumor regression and regrowth. Tumor samples from groups 5 and 6 were collected 3 hours post last dose depending on available tumor sizes. All procedures performed on these animals were in accordance with regulations and established guidelines and were reviewed and approved by Pfizer's Institutional Animal Care and Use Committee.

(iii) Data Interpretation: For each experiment, calculations were performed and graphs created in Microsoft Excel and GraphPad Prism version 7.02 respectively. The tumor volume was calculated as $0.5 \times length \times width^2$. Tumor growth inhibition (TGI) was determined by the formula: % TGI=$[1-(Vt_x-Vt_0/Vc_x-Vc_0)] \times 100$, where Vc, Vt are the geometric means of control and treated groups. X=day X on study and 0=initial day of dosing.

ELISA Assay:
(i) Histone Extraction: Histone extraction was performed using the EpiQuick Histone Extraction Kit (Epigentek OP0006). Frozen tumor samples were cut and homogenized using cold mortar and pestle on dry-ice. The homogenized mixture was transferred to a 1.5 mL tube in 1x Pre-Lysis Buffer (200 mg/mL) containing phenylmethylsulfonyl fluoride (PMSF). Samples were gently mixed, incubated on ice for 15 minutes, and spun down at 3,000 rpm for 5 minutes at 4° C. The tissue pellet was resuspended in 3 volumes (approximately 200 μL per 100 mg of tissue) of lysis buffer from the Histone Extraction Kit, incubated on ice for 30 minutes, and spun down at 12,000 rpm for 5 minutes at 4° C. Balance-DTT buffer was prepared by adding DTT Solution to balance buffer at a 1:500 ratio. The supernatant (containing acid soluble proteins) was transferred to a new 1.5 mL tube and 0.3 volumes of Balance-dithiothreitol (DTT) buffer from the Histone Extraction Kit were immediately added to each sample. The tumor lysate was briefly sonicated for 4 cycles (30 seconds on and 30 seconds off) at high intensity using the Bioruptor Plus (Diagenode #601020001). Extracts were aliquoted and stored at −20° C. (short term) or −80° C. (long term). Protein concentration was quantified using the Coomassie Plus (Bradford) Assay Kit (Thermo #23236).

(ii) H3K27Me3 and Me2 ELISA Assay: Histone extracts were diluted to a final concentration of 400 ng (or 800 ng) in 100 μL of coating buffer (phosphate buffered saline (PBS) containing 0.05% bovine serum albumin (BSA)). Four hundred (400) ng (or 800 ng) of each sample was added per well in duplicate in a 96-well assay microplate (Corning Costar), sealed tightly, and incubated overnight at 4° C. The following day, the wells in each plate were washed 3 times with 300 μl wash buffer (PBS, 0.05% Tween 20) and then blocked with 300 μL of blocking buffer (PBS, 0.05% Tween 20, 2% BSA) for 2 hours at room temperature. Following another round of washing with wash buffer (PBS, 0.05% Tween 20), 100 μL of detection antibody (Cell Signaling #9733 H3K27Me3 diluted 1:2000 in blocking buffer; Cell Signaling #9728 H3K27Me2 diluted 1:2000 in blocking buffer; ABCAM ab1791 total histone H3 diluted 1:5000 in blocking buffer) was added to each well of the respective plates and incubated at room temperature for 1.5 hours. Following another round of washes with wash buffer (PBS, 0.05% Tween 20), 100 μL of secondary antibody (anti-Rb-IgG-HRP, Cell Signaling 7074) diluted 1:2000 (H3K27Me3 and Me2) or 1:10,000 (total H3) was added to each well and the plate was incubated at room temperature for 1.5 hours. Following another round of washes with wash buffer (PBS, 0.05% Tween 20), detection was carried out by adding 100 μl of TMB Substrate (Thermo Scientific, N301) to each well, incubating the plate for 10 minutes, adding 100 μl of Stop Solution (0.16 M sulfuric acid, freshly prepared or purchased from Thermo Scientific N600) to each well, shaking gently, and reading absorbance at 450 nm. Data was analyzed using GraphPad Prism version 7.02. P-values were determined using one-way ANOVA (Tukey's multiple comparisons test).

Example 1—Antiproliferative Effect of Compound 1 in DMS114 SCLC Cells

The activity of Compound 1 against EZH2 was evaluated in DMS114 SCLC cells containing wild-type EZH2. EZH2 inhibitor activity was determined in the cells by measurement of the relative amount of cellular H3K27Me3 levels. DMS114 cells were treated with the indicated concentrations of Compound 1 for 3 days and H3K27Me3 levels were measured using an in-cell western assay described above. The results are shown in Table 2 and FIG. 1. FIG. 1 is representative of 5 independent biological replicate experiments. Following 3 days of treatment with a concentration range from 3 μM to 0.1 nM, Compound 1 demonstrated dose-dependent H3K27Me3 inhibition with a cellular mean $IC_{50}$ of 9.48 nM.

Figure 2:
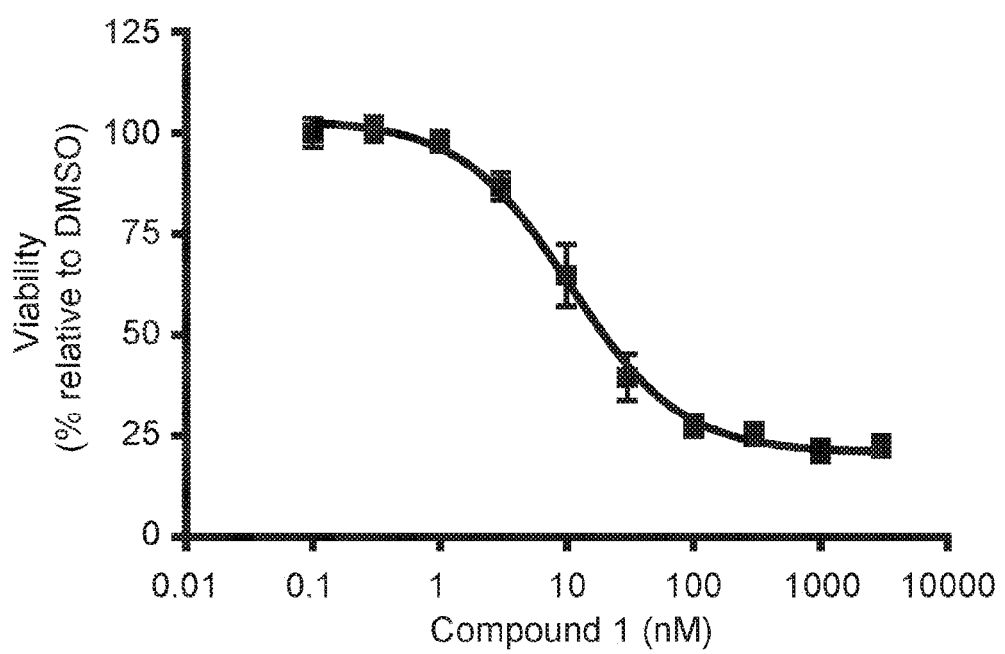
FIG. 2: Inhibition of proliferation by Compound 1 of DMS114 SCLC Cells. DMS114 SCLC cells were treated with different concentrations of Compound 1 for 19 days. Each data point represents % viable cells at a given compound concentration normalized to DMSO (Mean±SD; n=6). Figure is representative of 6 independent biological replicate experiments.

The activity of Compound 1 in inhibiting cell proliferation of EZH2-WT DMS114 SCLC cells was also assessed using the cell proliferation assay for DMS114 SCLC cells described above. DMS114 cells were treated with different concentrations of Compound 1 using a 10-point dose curve (1:3 dilution) with 3 μM to 0.1 nM for 17-21 days and then assessed for cell viability. The results are shown in Table 2 and FIG. 2. FIG. 2 is representative of 6 independent biological replicate experiments. The results indicated that Compound 1 demonstrated strong dose-dependent inhibition of cell proliferation in DMS114 cells with a mean $IC_{50}$ of 18.8 nM.

TABLE 2

Cellular Potency of Compound 1 in Inhibition of H3K27Me3 and Cell Proliferation in DMS114 Cells

| Cell line | Cancer Type | H3K27Me3 IC50 ± SD (nM) (n) | Proliferation IC50 ± SD (nM) (n) |
|---|---|---|---|
| DMS114 | SCLC | 9.48 ± 5.34 (5) | 18.8 ± 13.2 (6) |

IC50 = Half maximal inhibitory concentration;
SD = Standard deviation

Figure 3:
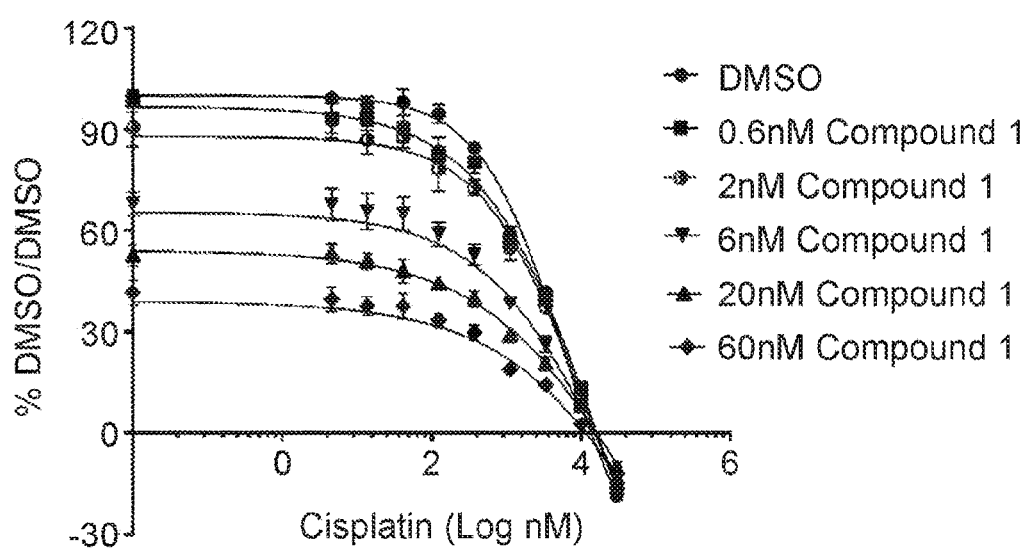
FIG. 3: Compound 1 displays synergistic effects in combination with cisplatin in DMS114 SCLC cells. Cells were pre-treated with Compound 1 for 9 days followed by co-treatment with cisplatin for 4 days. Data was normalized to untreated DMSO/DMSO sample and represented as % of untreated sample. The data was analysed using Loewe additivity combination model.
Figure 4:
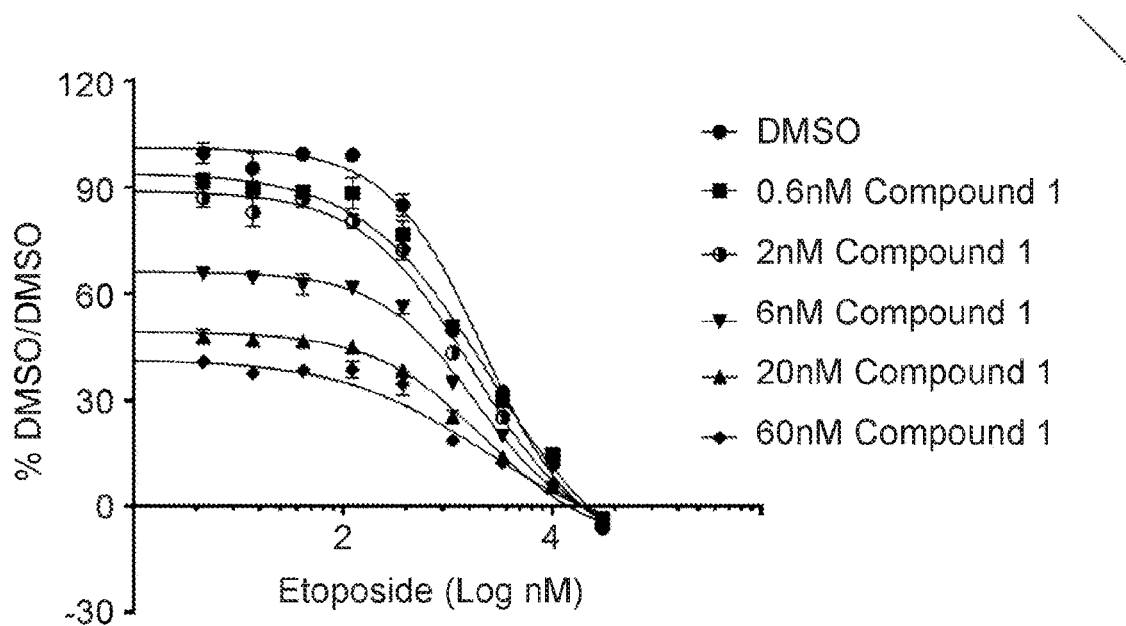
FIG. 4: Compound 1 displays synergistic effects in combination with etoposide in DMS114 SCLC cells. Cells were pre-treated with Compound 1 for 9 days followed by co-treatment with etoposide for 4 days. Data was normalized to untreated DMSO/DMSO sample and represented as % of untreated sample. The data was analysed using Loewe additivity combination model.
Figure 4:
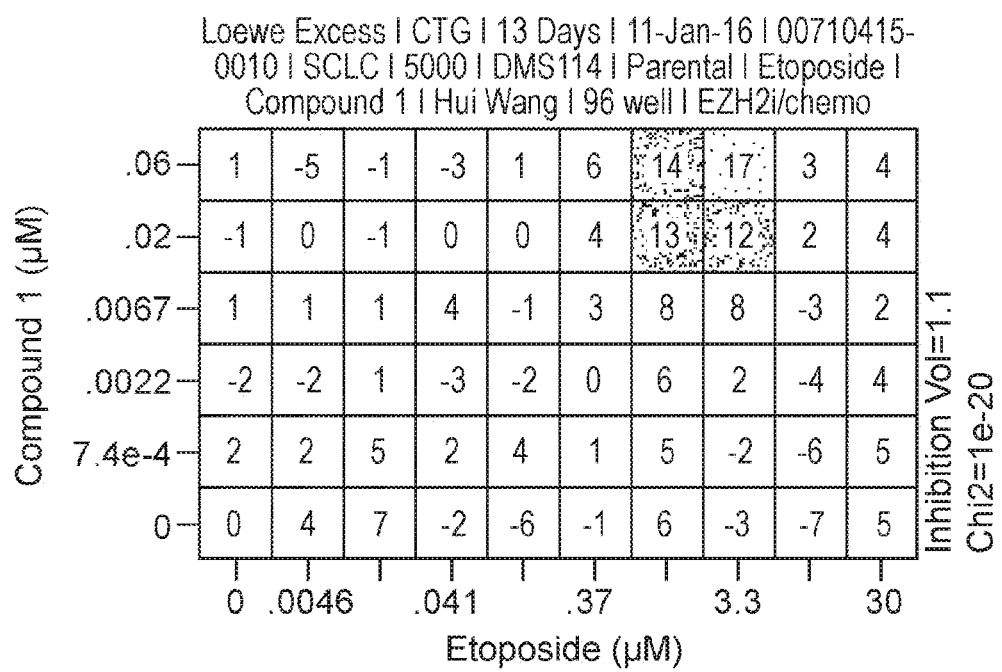

Example 2—Evaluation of Antiproliferative Synergy for Combination of Compound 1+SCLC Standard of Care Agents Cisplatin or Etoposide In view of the strong efficacy observed with Compound 1 in inhibiting the growth of SCLC DMS114 cell line, Compound 1 in combination with current standard of care chemotherapy agents was investigated. The experiments were conducted using the cell growth inhibition assay for DMS114 SCLC cells in accordance with the method described above, and the results are show in FIGS. 3 and 4. FIG. 3 shows an $IC_{50}$ curve for Compound 1 dosed alone and in dosed in combination with cisplatin. FIG. 4 shows an $IC_{50}$ curve for Compound 1 dosed alone and in combination with etoposide. These experiments show that prior treatment with Compound 1 strongly increased anti-proliferative effects of both of either cisplatin or etoposide in DMS114 cells. FIGS. 3 and 4 also show the results of further analysis of the combination data using Loewe Additivity (ADD) model as described above. This analysis showed that the level of growth inhibition achieved with doses above $IC_{50}$ for both compounds was stronger than which would be expected if the effect of both compounds was additive.

Figure 5A:
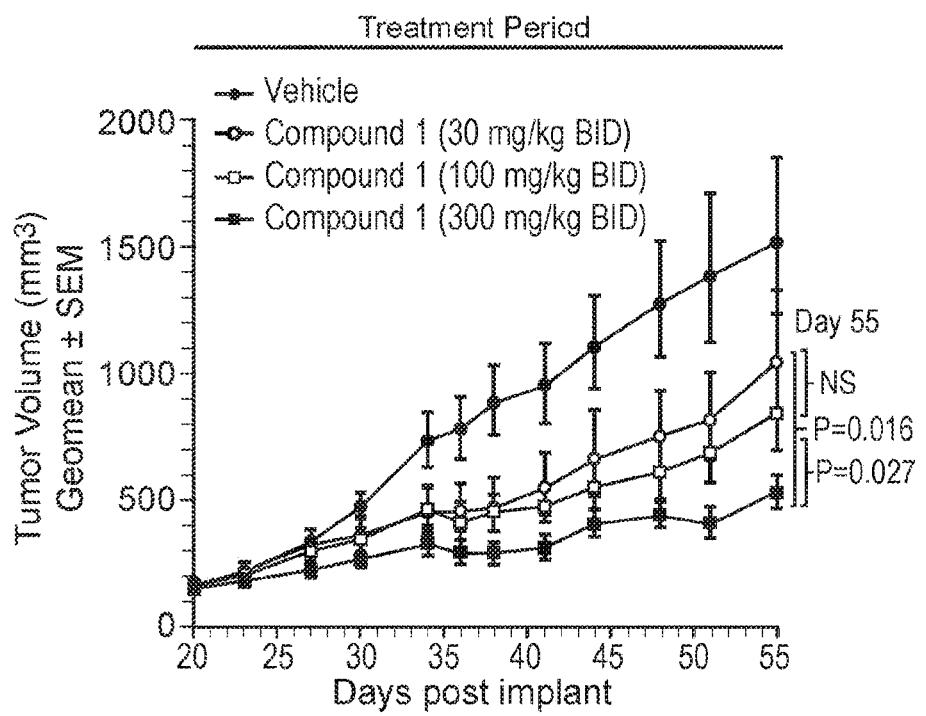
FIG. 5: Anti-tumor efficacy of single-agent Compound 1 in the DMS114 SCLC Xenograft model. Growth curves of DMS114 tumors and TGI values for Compound 1 treatment arms (geomean±SEM). Randomisation and treatment started on Day 20 after implant in female NOD/SCID mice. P values: 2-tailed t-test. 30 and 100 mg/kg BID treated groups showed significantly less TGI than the 300 mg/kg BID group. Percent body weight changes are shown relative to the treatment start on Day 20 (mean±SEM).
Figure 5B:
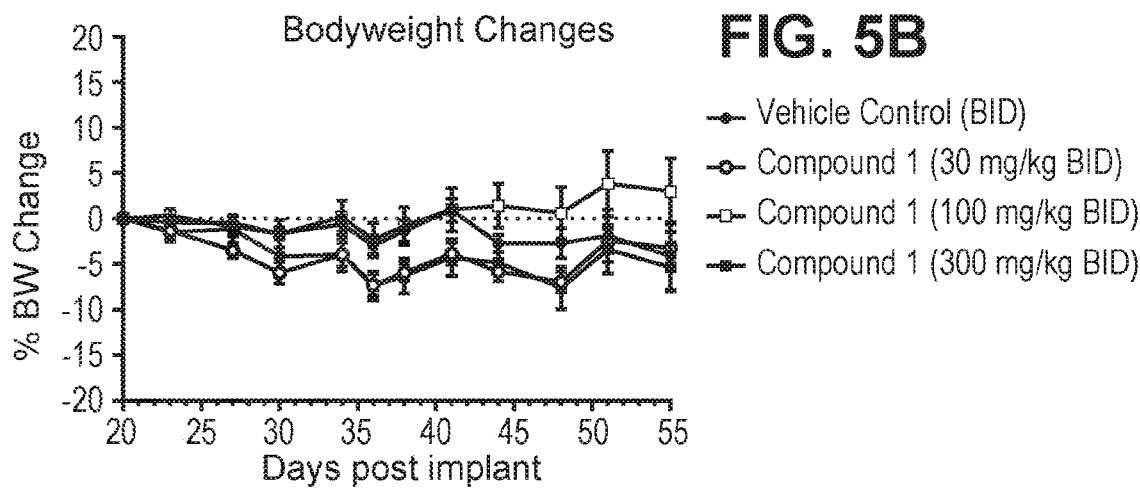

Example 3—Single Agent Compound 1 Inhibits Tumor Growth In-Vivo in DMS114 SCLC Xenograft Model Anti-tumor efficacy of Compound 1 was tested in vivo in the DMS114 SCLC xenograft model using the in vivo xenograft study protocol described above. The definition of the study arms, dosing regimes and routes of administration are summarized in Table 1. The results are shown in FIG. 5. Compound 1 showed a dose-dependent efficacy response with a maximum tumor growth inhibition (TGI) of 69% to 79% at 300 mg/kg twice daily (BID). On Day 20 post tumor cell implant, mice were randomized into treatment groups based on tumor size. The geometric mean for the tumor sizes at randomization in each group was about 160 mm³. From the results shown in FIG. 5 it can be seen that Compound 1 dosed 100 mg/kg BID and 300 mg/kg BID both showed significant anti-tumor benefit vs the control group that was dosed with vehicle. Demonstrating dose dependent efficacy, there was a significant TGI benefit for the highest 300 mg/kg BID dose vs the 30 mg/kg BID and 100 mg/kg BID treatments, (Day 55; 2-tailed t-test). No complete tumor regressions were observed in the Compound 1 monotherapy arms. Compound 1 was well tolerated with limited body-weight loss.

Figure 6A:
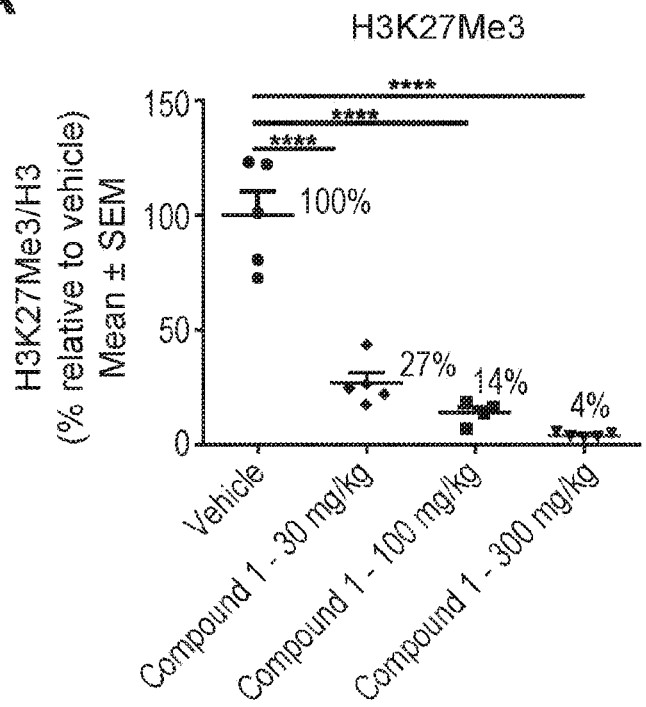
FIG. 6: Dose-dependent Inhibition of H3K27Me3 and Me2 by Compound 1 in the DMS114 SCLC Xenograft Model. Modulation of (A) H3K27Me3 and (B) H3K27Me2 in DMS114 tumors treated with different doses of Compound 1. Histones were extracted from snap-frozen tumors harvested at Day 55 and methylation levels were assessed using ELISA assay (Mean±SEM; *ns P >0.05; *P≤0.05; P≤0.01; *P≤0.001; ****P≤0.0001).
Figure 6B:
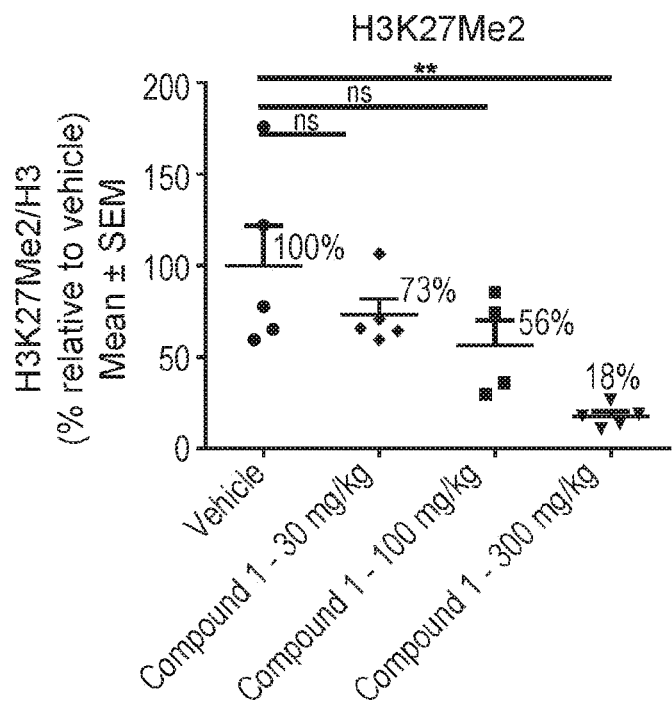

Example 4—Single Agent Compound 1 Shows Dose-Dependent Biomarker Inhibition of H3K27Me3 and Me2 In-Vivo in the DMS114 SCLC Xenograft Model The in vivo activity of Compound 1 against EZH2 in the DMS114 SCLC xenograft model was determined by measurement of the relative amount of cellular H3K27Me3 and Me2 levels with ELISA using the tumor tissue samples harvested at Day 55 from the study described in Example 3 above. The results are shown in FIG. 6. Compound 1 displayed dose-dependent inhibition of H3K27Me3 and Me2 in the tumor samples with a maximum inhibition of 96% and 82% for H3K27Me3 and Me2, respectively, at 300 mg/kg BID.

Figure 7A:
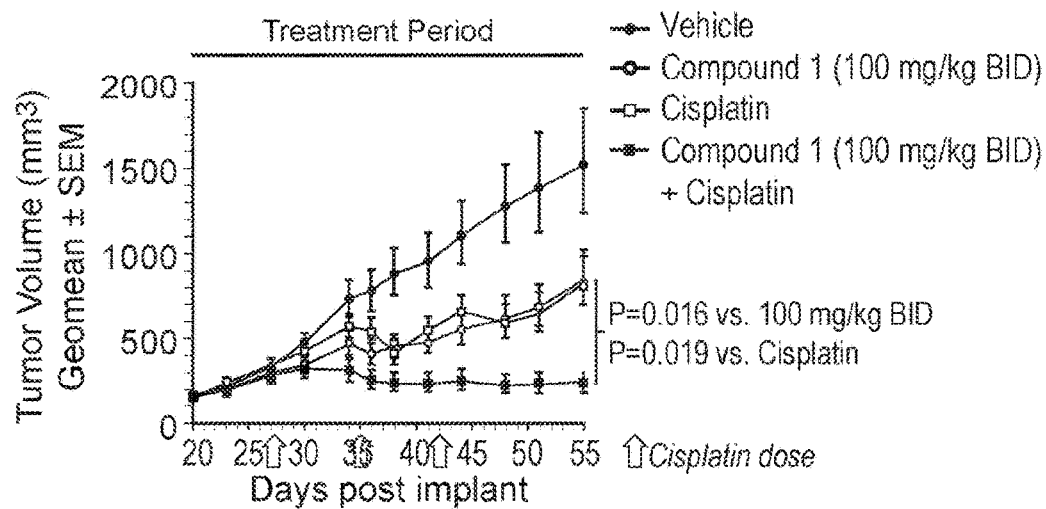
FIG. 7: Combinatorial Anti-tumor Benefit of Cisplatin with Compound 1 in the DMS114 SCLC Xenograft Model. A. Growth curves of DMS114 tumors and TGI values for Compound 1 and cisplatin treatment arms (geometric mean±SEM). Randomization and treatment start on Day 20 after implant in female NOD/SCID mice. P values: 2-tailed t-test. Compound 1 100 mg/kg BID and cisplatin monotherapy groups showed significantly less TGI than the combination treatment group. B. Percent body weight changes are shown relative to the treatment start on Day 20 (mean±SEM). C. Individual tumor growth curves for the combination treatment group. Tumor volume regressions were seen in 50% of the mice treated with the combination relative to the tumor size at treatment start (shown with grey lines/open circles).
Figure 7B:
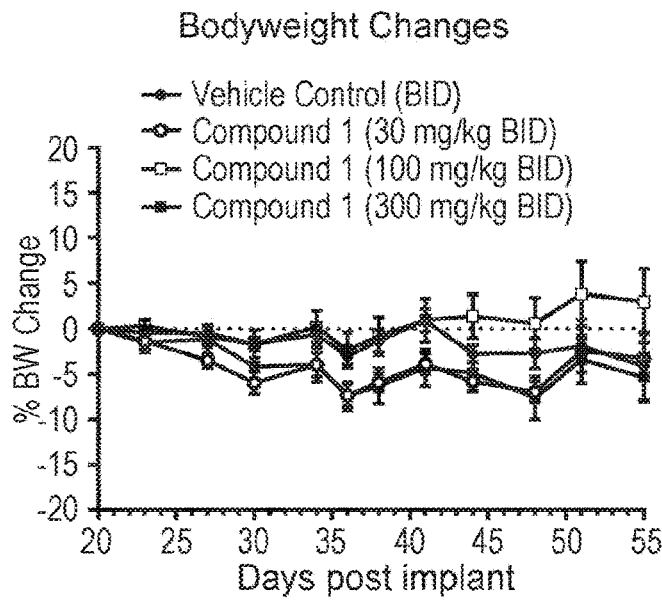
Figure 7C:
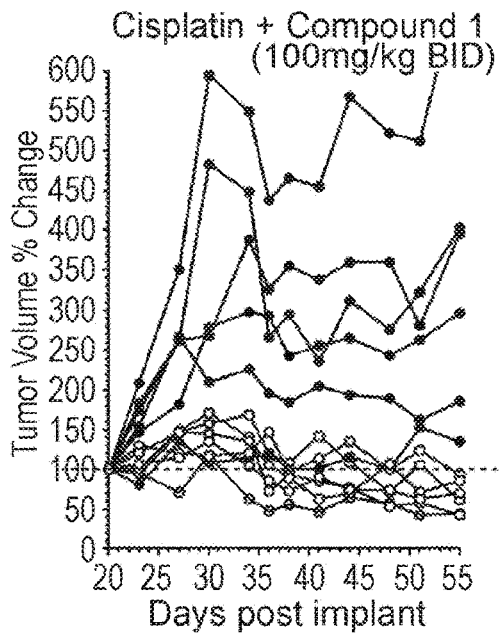

Example 5—Compound 1 Shows Combinatorial Anti-Tumor Activity Benefit with Cisplatin in the DMS114 SCLC Xenograft Model Anti-tumor efficacy of Compound 1 in combination with cisplatin was tested in vivo in an EZH2-WT DMS114 SCLC xenograft model using the in vivo xenograft study protocol described above. The definition of the study arms, dosing regimes and routes of administration are summarized in Table 1. The results are shown in FIG. 7. On Day 55, in the cisplatin and Compound 1 single treatment groups, all tumors had progressed and were larger than at treatment start, even though intermittent tumor shrinkages were observed following cisplatin administration. By contrast, in the combination group, 6 out of 12 tumors had regressed compared to the starting tumor burden. By Day 55 the combination treatment resulted in a TGI of 95% and was significantly more efficacious than monotherapy with either cisplatin (TGI of 51%; P=0.019 vs cisplatin) or with Compound 1 (TGI of 50%; P=0.016 vs 100 mg/kg Compound 1). Cisplatin treatment was stopped after the 3rd dose in both single-agent and combination arms, since it caused body weight loss in mice (FIG. 7). Compound 1 single agent treatments were well tolerated (FIG. 7), while the Compound 1+cisplatin combination showed body weight loss that was significantly more pronounced than in the cisplatin monotherapy treatment group (P<0.05 for all measurements on Day 27 and later; 2-tailed t-test).

To assess the effect of EZH2 inhibition on durability of response, the cisplatin monotherapy group and the combination therapy group were kept on study post Day 55. In both of these treatment arms the last cisplatin treatment had been given on Day 42. In the combination arm only dosing of monotherapy Compound 1 was continued as a maintenance therapy for an additional 3 weeks (without cisplatin dosing). The results are shown in FIG. 7. The maintenance dose of Compound 1 sustained tumor regression in the combination arm for a further 34 days following cisplatin discontinuation while all the tumors in the cisplatin monotherapy arm, who were receiving no further treatment, progressed. In the combination arm, and after cisplatin treatment had stopped, the body weights recovered completely during maintenance dosing with Compound 1, indicating that minimal toxicity resulted from Compound 1 maintenance dose (FIG. 7).

Figure 9:
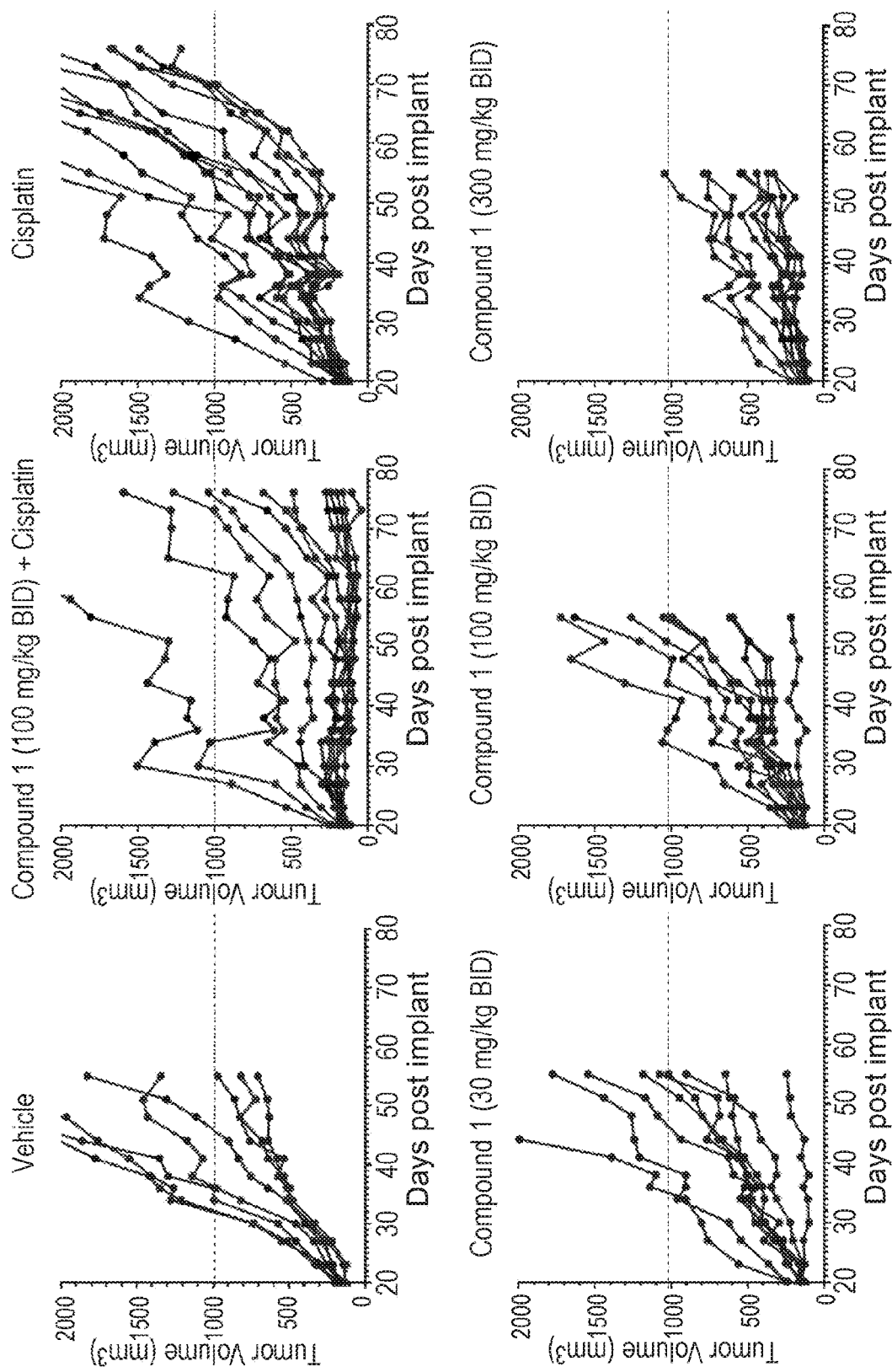
FIG. 9: Individual Tumor Growth Curves in the DMS114 SCLC Xenograft Model. Randomization on Day 20 after implant (107 cells in 0.1 mL PBS with 50% matrigel) in female NOD/SCID mice.

Further, from the data shown in FIGS. 8 and 9 it can be seen that the cisplatin and Compound 1 combination provided a significant survival benefit vs either vehicle, or Compound 1 or cisplatin monotherapies. For the survival readout, the maximum tumor burden was set at 500 mm³. The 100 mg/kg BID Compound 1 group and the cisplatin monotherapy groups did not reach the P<0.05 significance level in the Log-rank test (Mantel-Cox) vs. the vehicle control group. The median survival increased to 74.5 days in the combination vs 34 days in the vehicle, 39 days in the 100 mg/kg BID Compound 1 and 37.5 days in the cisplatin groups.

In summary, Compound 1 demonstrated dose dependent inhibition of tumor growth in vivo in the DMS114 SCLC xenograft model. The dose dependent inhibition also correlated with potent inhibition of H3K27Me3 and Me2 biomarkers. Based on the minimal observed body weight changes, it was concluded that dosing with Compound 1 was tolerated in mice. Dosing with a combination of Compound 1 with first line standard of care cisplatin significantly increased both the anti-tumor efficacy and durability of the anti-tumor response when compared with cisplatin monotherapy resulting in a significant survival benefit. Further the non-clinical studies described herein demonstrate that Compound 1 inhibits EZH2 catalytic activity in vivo, as measured by H3K27Me3 and Me2 inhibition, inducing strong inhibition of tumor growth both as a single agent and in combination with cisplatin in this DMS114 SCLC xenograft model.

Example 6—Antiproliferative Effect of Compound 1 in Additional SCLC Cell Lines

Figure 10:
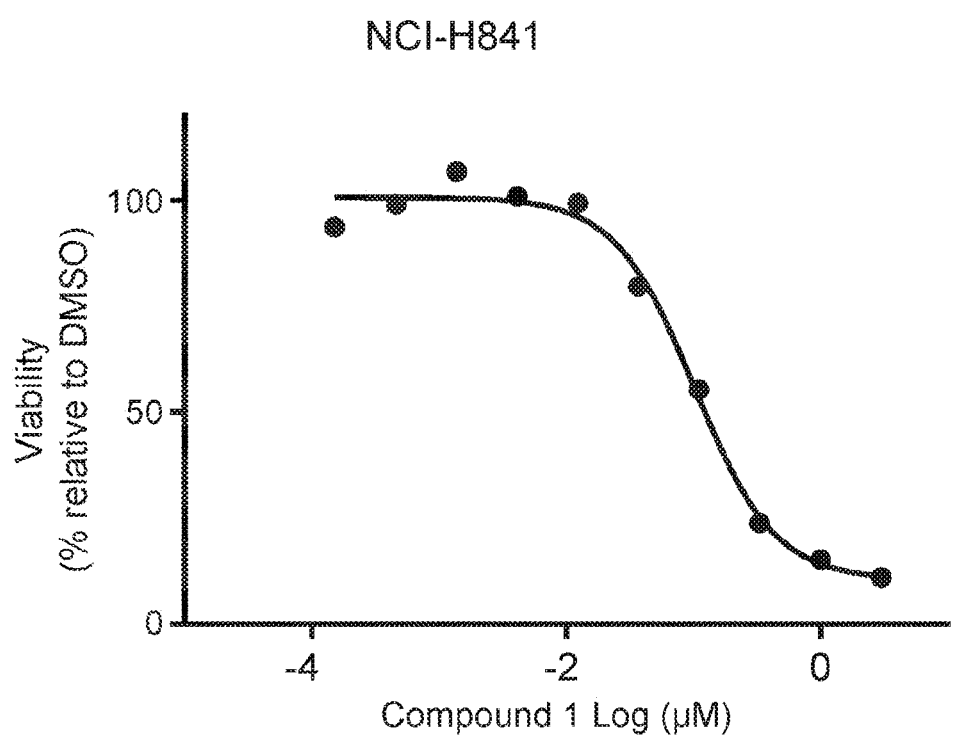
FIG. 10: Inhibition of proliferation by Compound 1 of H841 SCLC Cells. H841 SCLC cells were treated with different concentrations of Compound 1 for 21 days. Each data point represents % viable cells at a given compound concentration normalized to DMSO (Mean±SEM; n=3 technical replicates). Figure is representative of 2 independent biological replicate experiments.
Figure 11:
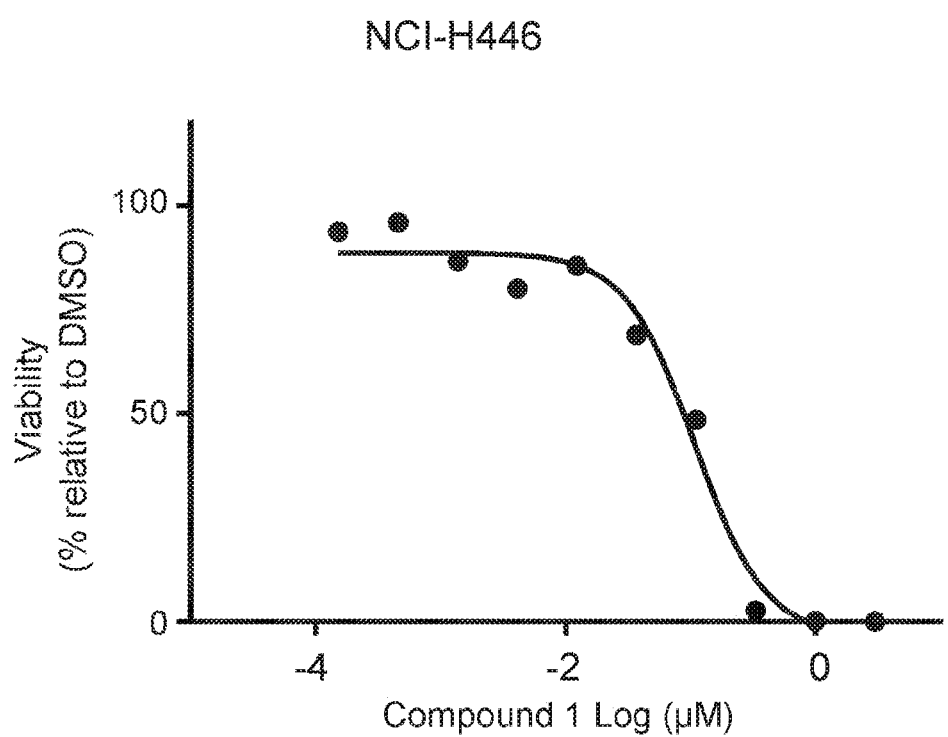
FIG. 11: Inhibition of proliferation by Compound 1 of H446 SCLC Cells. H446 SCLC cells were treated with different concentrations of Compound 1 for 21 days. Each data point represents % viable cells at a given compound concentration normalized to DMSO (Mean±SEM; n=3 technical replicates).
Figure 12:
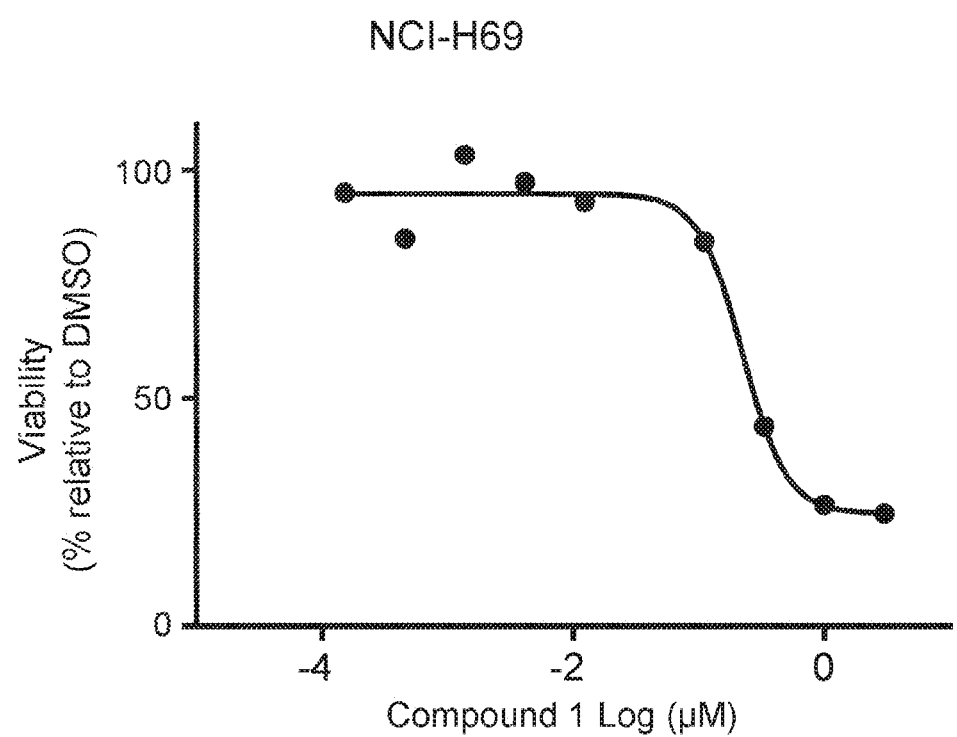
FIG. 12: Inhibition of proliferation by Compound 1 of H69 SCLC Cells. H69 SCLC cells were treated with different concentrations of Compound 1 for 21 days. Each data point represents % viable cells at a given compound concentration normalized to DMSO (Mean±SEM; n=3 technical replicates).

Based on the strong activity observed with Compound 1 in DMS114 cells (see example 1 above), the antiproliferative activity of Compound 1 was also tested in 3 additional SCLC cell lines, namely H841, H446 and H69 using the cell proliferation assay described above. Each cell line was treated with different concentrations of Compound 1 using a 10-point dose curve (1:3 dilution in DMSO) with 3 µM to 0.1 nM for 21 days and then assessed for cell viability. The results are shown in FIG. 10 (H841), FIG. 11 (H446) and FIG. 12 (H69). Following 21 days of treatment, Compound 1 demonstrated strong dose-dependent inhibition of cell proliferation with a mean $IC_{50}$ of 73.15 nM in H841 cell line; 108.6 nM in H446 cell line; and 224.1 nM in H69 cell line.

Figure 13:
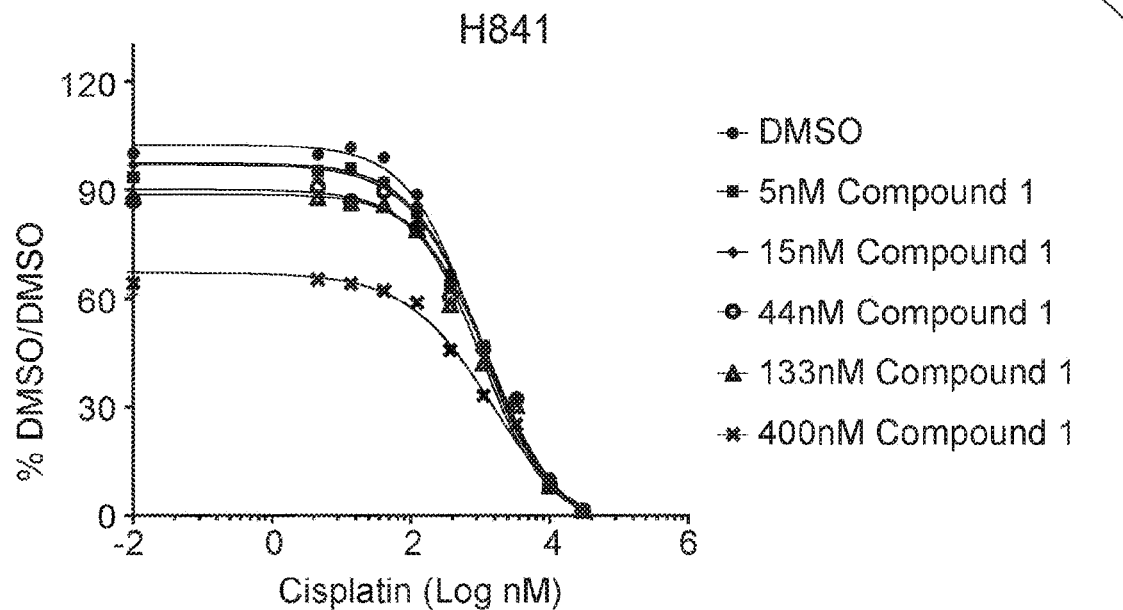
FIG. 13: Compound 1 displays synergistic/additive effects in combination with cisplatin in H841 SCLC cells. H841 cells were pre-treated with Compound 1 for 9 days followed by co-treatment with cisplatin for 4 days. Data was normalized to untreated DMSO/DMSO sample and represented as % of untreated sample. The data was analysed using Loewe additivity combination model.
Figure 13:
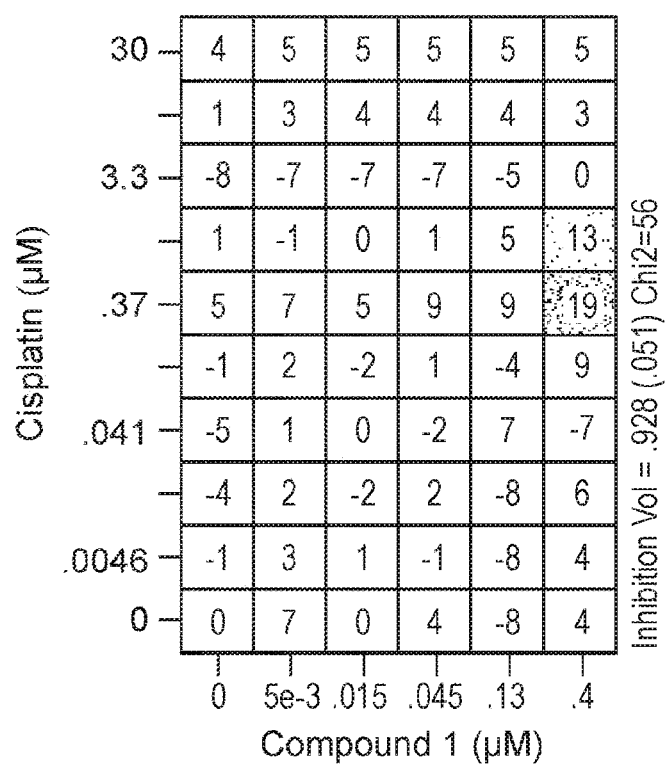
Figure 14:
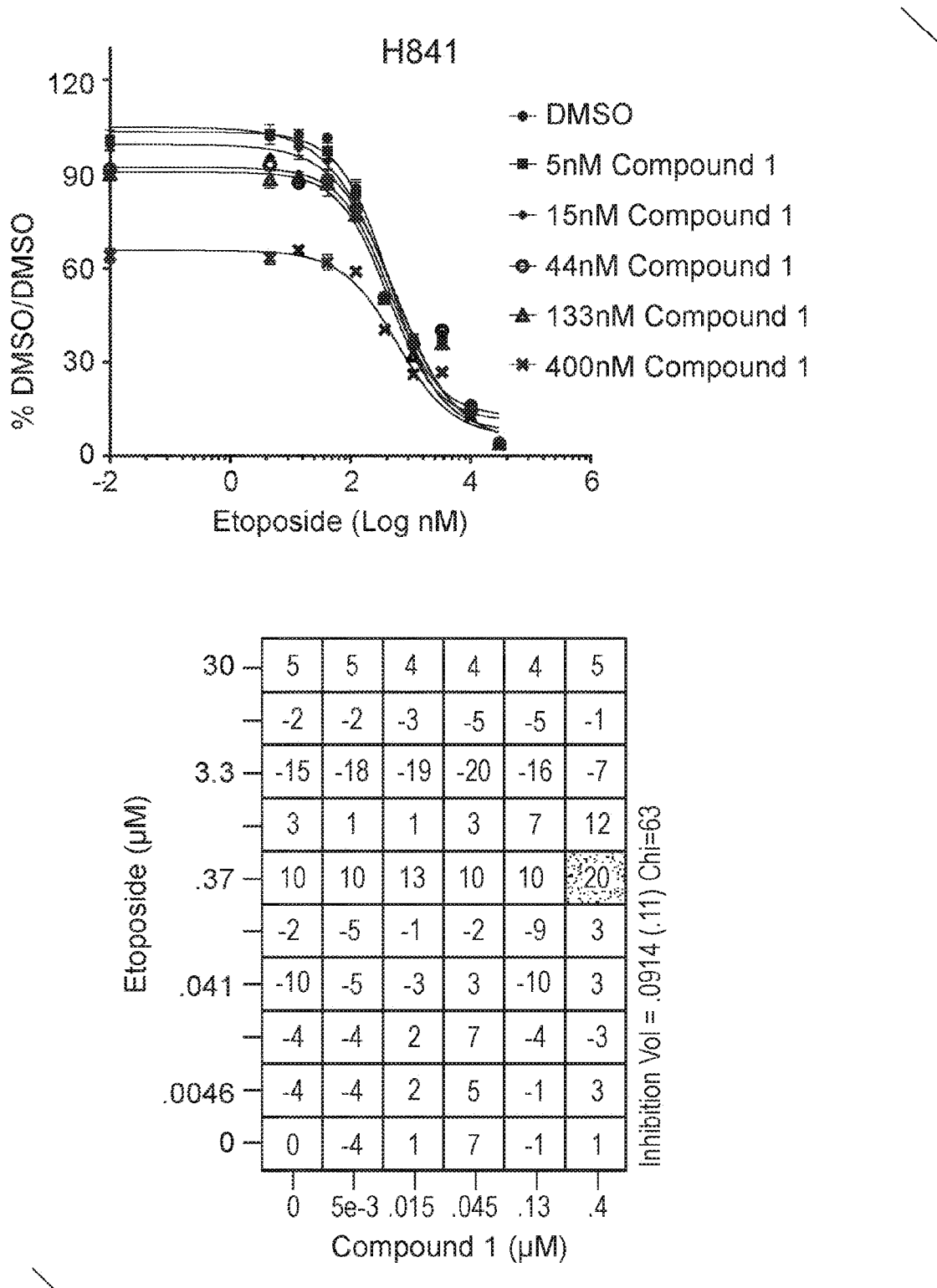
FIG. 14: Compound 1 displays synergistic/additive effects in combination with etoposide in H841 SCLC cells. H841 cells were pre-treated with Compound 1 for 9 days followed by co-treatment with etoposide for 4 days. Data was normalized to untreated DMSO/DMSO sample and represented as % of untreated sample. The data was analysed using Loewe additivity combination model.
Figure 15:
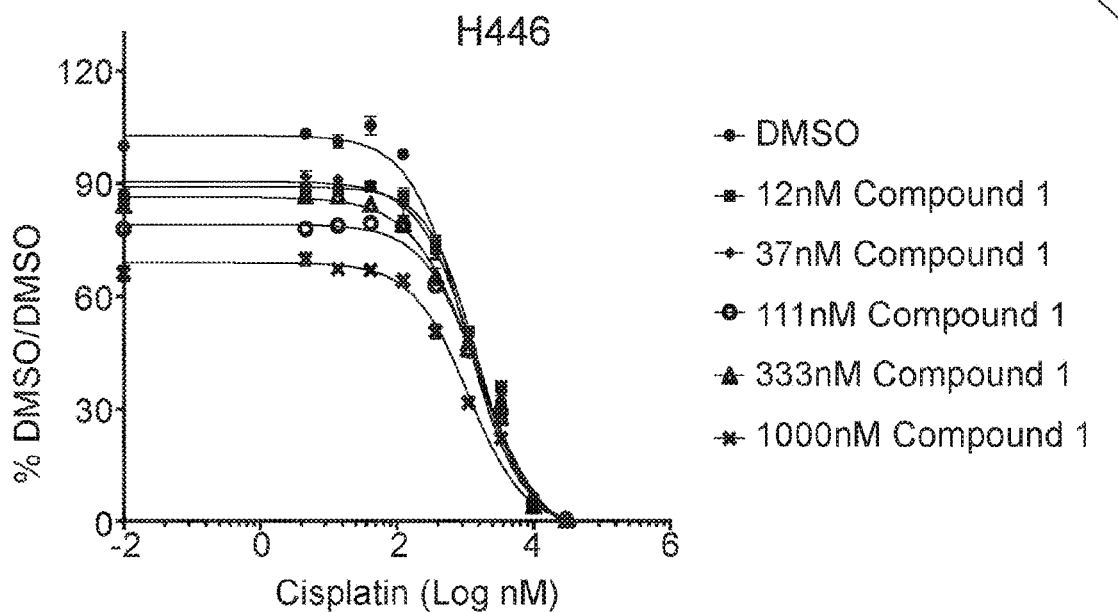
FIG. 15: Compound 1 displays synergistic effects in combination with cisplatin in H446 SCLC cells. H446 cells were pre-treated with Compound 1 for 9 days followed by co-treatment with cisplatin for 4 days. Data was normalized to untreated DMSO/DMSO sample and represented as % of untreated sample. The data was analysed using Loewe additivity combination model.
Figure 15:
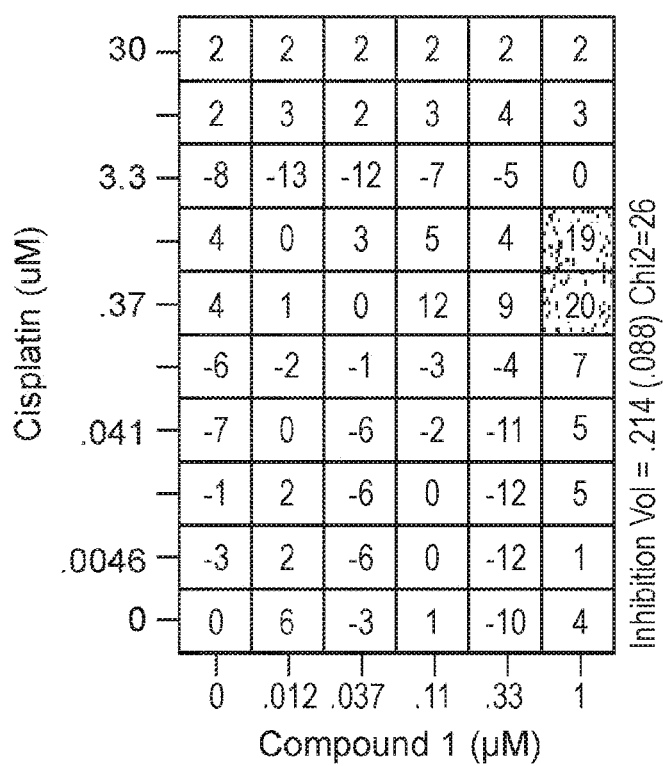
Figure 16:
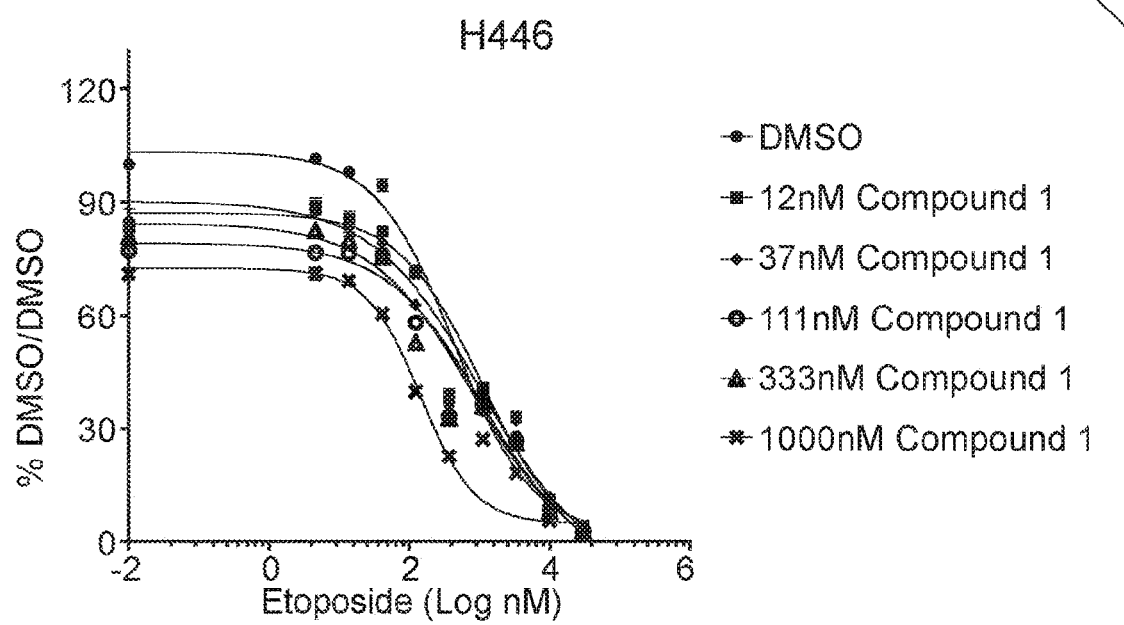
FIG. 16: Compound 1 displays synergistic effects in combination with etoposide in H446 SCLC cells. H446 cells were pre-treated with Compound 1 for 9 days followed by co-treatment with etoposide for 4 days. Data was normalized to untreated DMSO/DMSO sample and represented as % of untreated sample. The data was analysed using Loewe additivity combination model.
Figure 16:
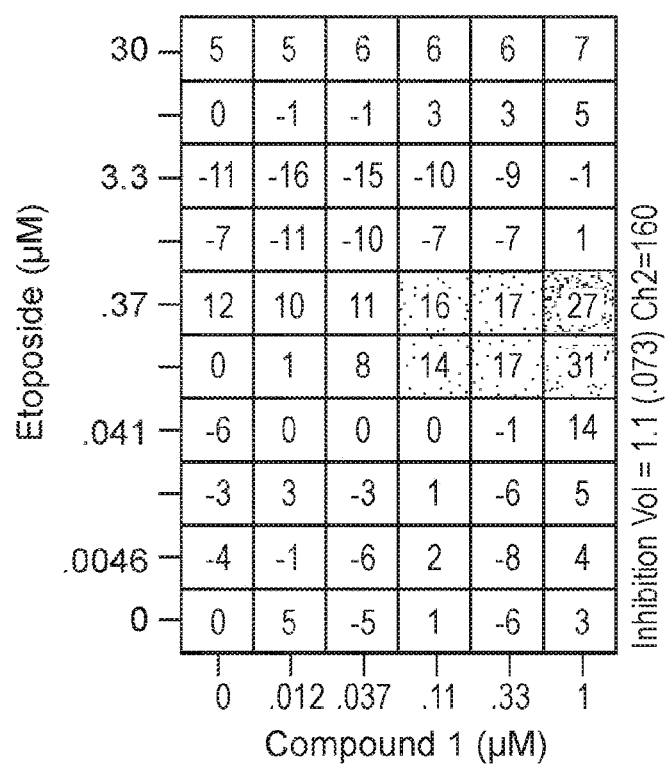
Figure 17:
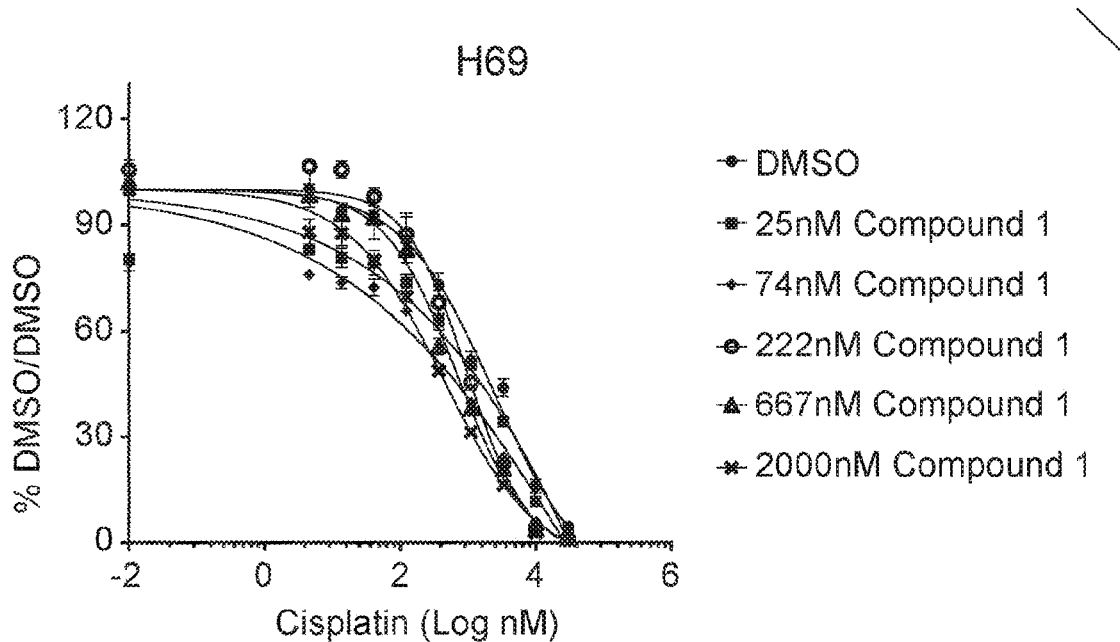
FIG. 17: Compound 1 displays synergistic effects in combination with cisplatin in H69 SCLC cells. H69 cells were pre-treated with Compound 1 for 9 days followed by co-treatment with cisplatin for 4 days. Data was normalized to untreated DMSO/DMSO sample and represented as % of untreated sample. The data was analysed using Loewe additivity combination model.
Figure 17:
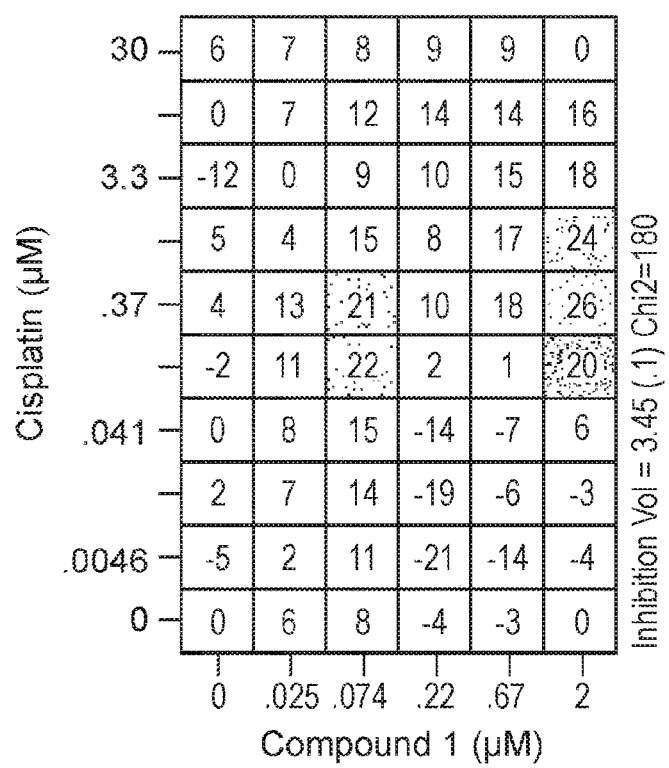
Figure 18:
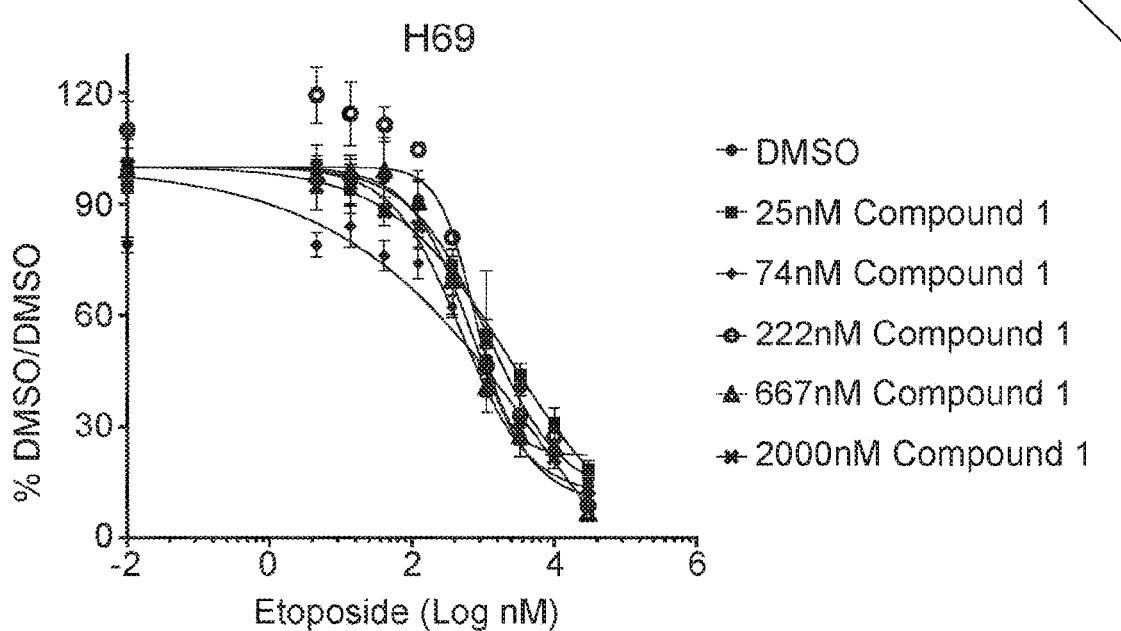
FIG. 18: Compound 1 displays synergistic effects in combination with etoposide in H69 SCLC cells. H69 cells were pre-treated with Compound 1 for 9 days followed by co-treatment with etoposide for 4 days. Data was normalized to untreated DMSO/DMSO sample and represented as % of untreated sample. The data was analysed using Loewe additivity combination model.
Figure 18:
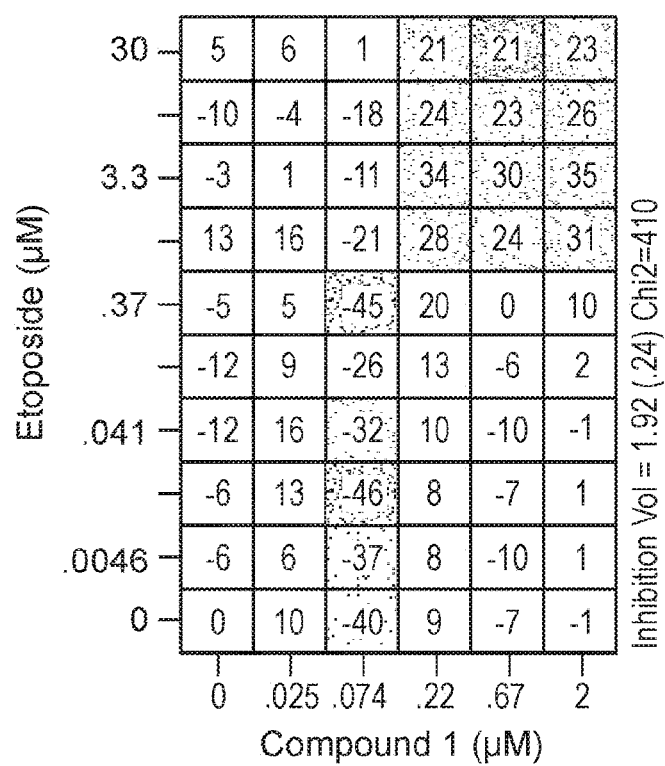

Example 7—Evaluation of Antiproliferative Synergy for Combination of Compound 1+SCLC Standard of Care Agents Cisplatin or Etoposide in H841, H446 and H69 Cell Lines In view of the strong efficacy observed with Compound 1 in inhibiting the growth of SCLC H841, H446 and H69 cell lines, a combination of Compound 1 with current standard of care chemotherapy agents cisplatin or etoposide was investigated. The experiments were conducted using the cell growth inhibition assay for H841, H446 or H69 SCLC cells in accordance with the method described above, and the results are shown in FIGS. 13 and 14 (H841 cell line); FIGS. 15 and 16 (H446 cell line) and FIGS. 17 and 18 (H69 cell line). FIGS. 13, 15 and 17 show an $IC_{50}$ curve for Compound 1 dosed alone and in combination with cisplatin. FIGS. 14, 16 and 18 show an $IC_{50}$ curve for Compound 1 dosed alone and in combination with etoposide. As with DMS114, these experiments show that prior treatment with Compound 1 strongly increased anti-proliferative effects of both of either cisplatin or etoposide in the H841, H446 and H69 cell lines.

FIGS. 13-18 also show the results of further analysis of the combination data using Loewe Additivity (ADD) model as described above. This analysis showed that the level of growth inhibition achieved with doses above $IC_{50}$ for both compounds was at least as strong or stronger than which would be expected if the effect of both compounds was additive.

Example 8—Compound 1 Induces Expression of SLFN11 in SCLC Cell Lines

Figure 19:
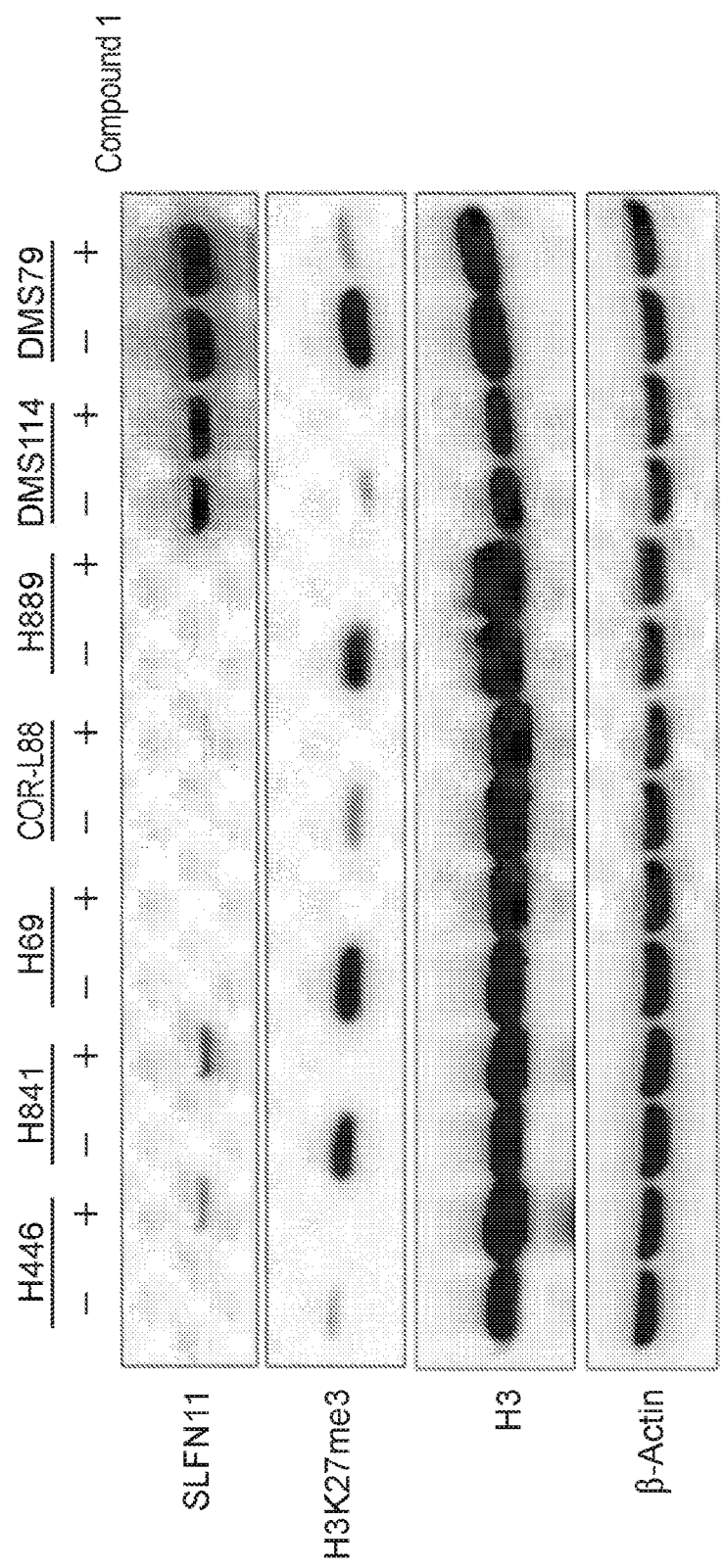
FIG. 19: Compound 1 induces SLFN11 expression in SCLC cell lines. SCLC cell lines were treated with 500 nM of Compound 1 for 7 days and SLFN11 expression was detected using Western Blotting.

To understand the potential mechanisms responsible for EZH2i synergy observed with chemotherapy agents, we assessed the effects of Compound 1 treatment on SLFN11 expression, a sensitizer to DNA damaging agents. Several SCLC cell lines were treated with 500 nM of Compound 1 for 7 days and changes in SLFN11 protein levels were assessed using western blotting according to the methodology described above. The results are shown in FIG. 19. These results indicate that strong induction of SLFN11 expression was observed in several cell lines upon treatment with Compound 1.

Figure 20:
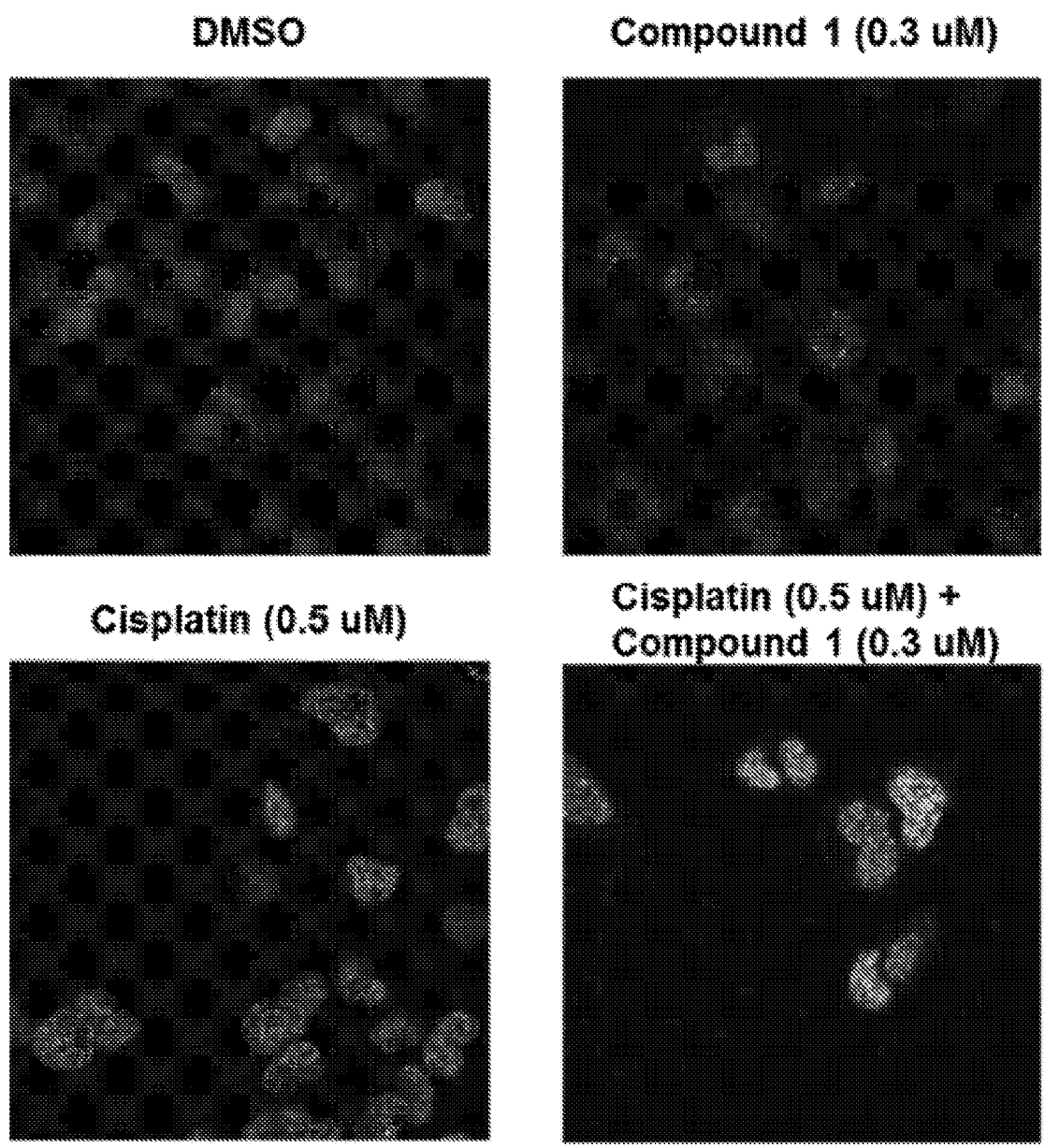
FIG. 20: Compound 1 in combination with cisplatin induces increased γ-H2AX foci in H841 SCLC cell line. H841 cells were pre-treated with Compound 1 for 7 days followed by co-treatment with cisplatin for 16 hours. Cells were then stained for γ-H2AX.
Figure 21:
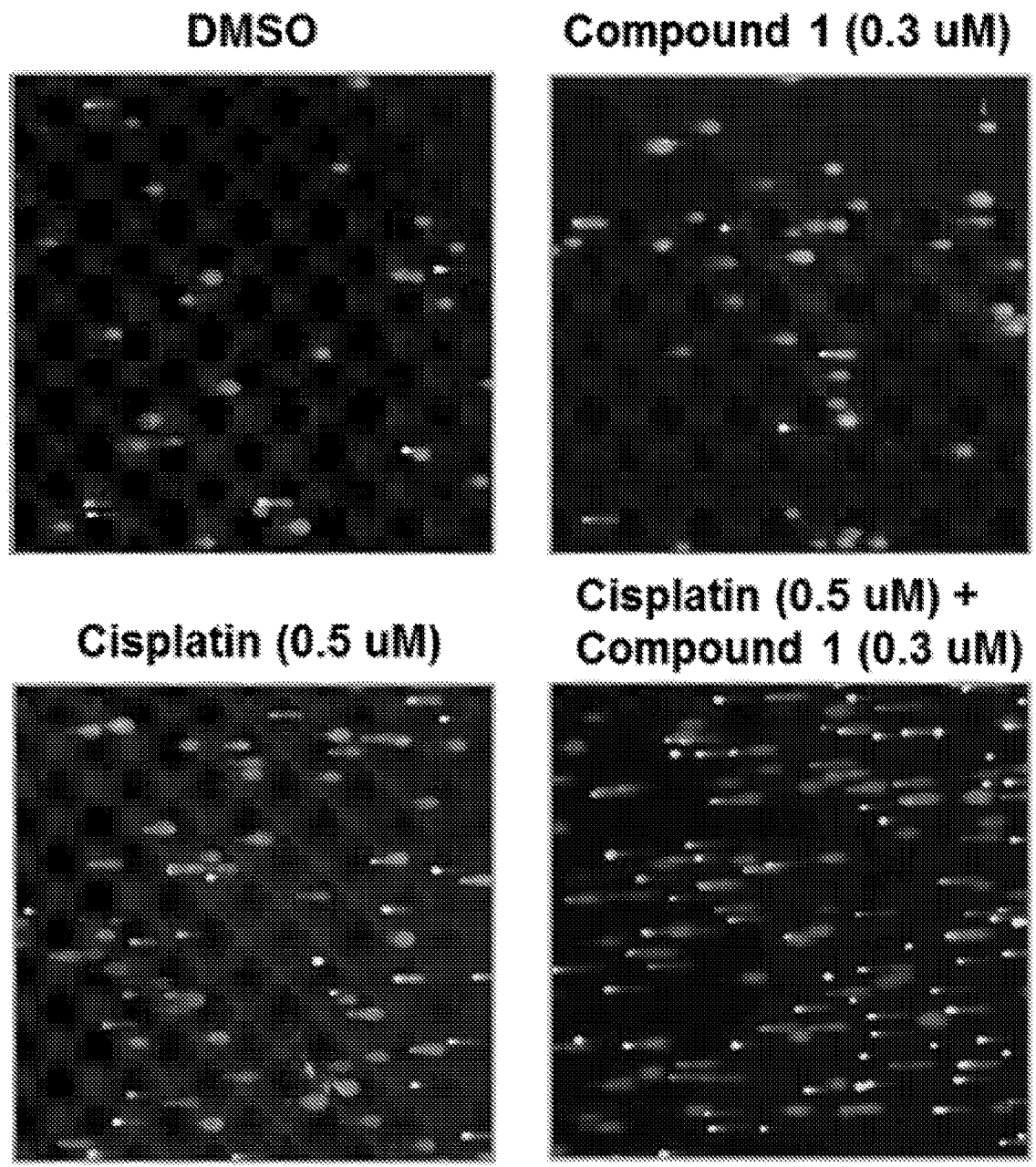
FIG. 21: Compound 1 in combination with cisplatin induces increased DNA damage in H841 SCLC cell line as indicated by COMET assay. H841 cells were pre-treated with Compound 1 for 7 days followed by co-treatment with cisplatin for 3 days. Cells were then analysed for DNA damage using the COMET assay.
Figure 22:
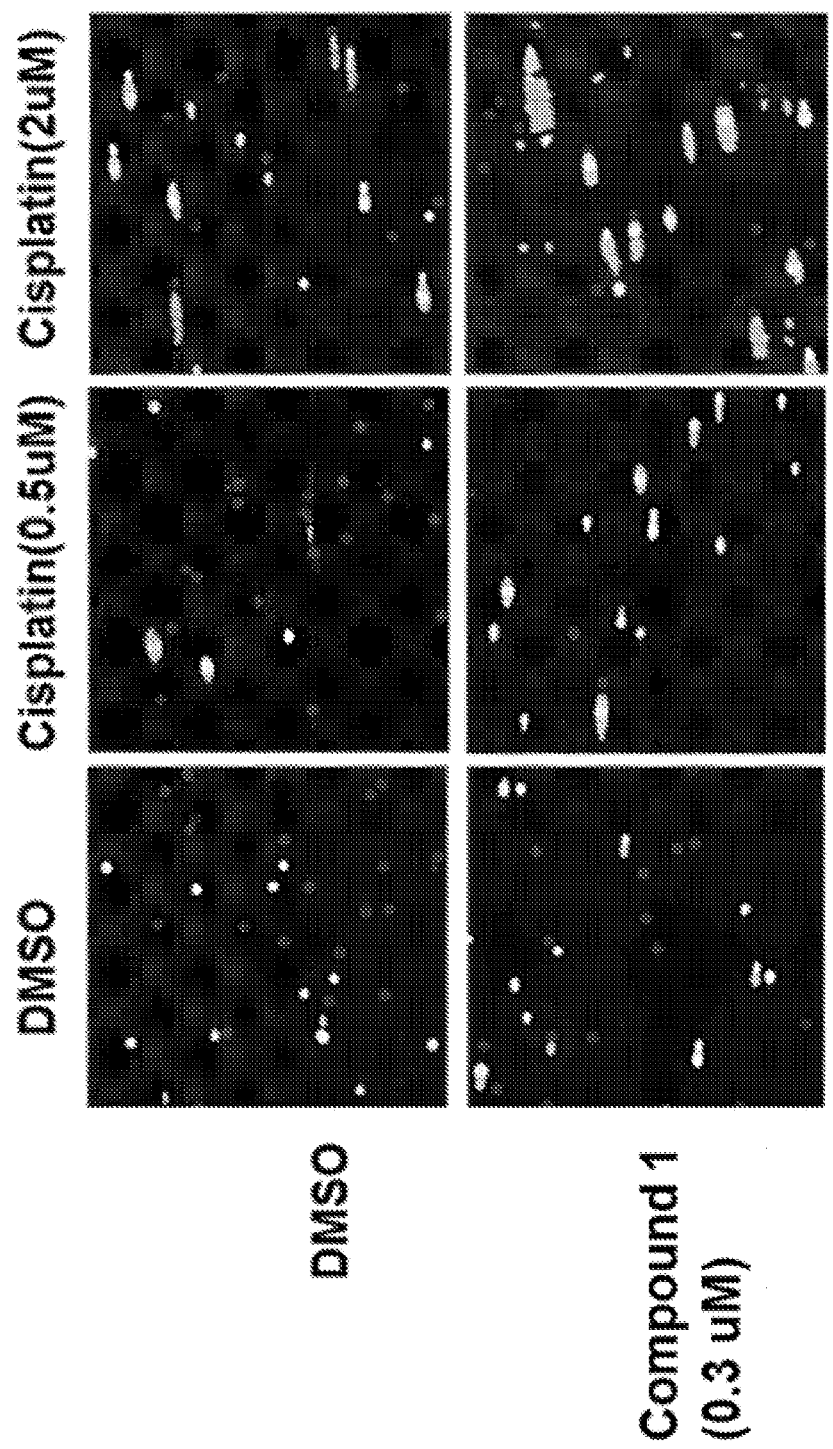
FIG. 22: Compound 1 in combination with cisplatin induces increased DNA damage in H69 SCLC cell line as indicated by COMET assay. H69 cells were pre-treated with Compound 1 for 7 days followed by co-treatment with cisplatin for 3 days. Cells were then analysed for DNA damage using the COMET assay.

Example 9—the Combination of Compound 1+SCLC Standard of Care Agent Cisplatin Induces Increased DNA Damage in SCLC Cell Lines The effect of Compound 1 in combination with chemotherapy agent cisplatin on DNA damage was assessed using either the DNA damage marker γ-H2AX staining or assessment of DNA damage with the COMET assay according to the methodology described above. The SCLC cell lines H841 or H69 were pre-treated with Compound 1 for 7 days, followed by co-treatment with cisplatin for either 16 hrs (γ-H2AX) or 3 days (COMET assay). The results are shown in FIGS. 20-22. In FIG. 20, the results from the H841 cell line indicate that a strong increase in γ-H2AX foci formation was observed in the cells treated with the combination when compared to those treated with either monotherapy. In FIG. 21, the results from the H841 cell line indicate that a strong increase in DNA damage (COMET assay) was observed in the cells treated with the combination when compared to those treated with either monotherapy. Similar results were achieved in the H69 cell line COMET assay (see FIG. 22).

All publications and patents/patent applications cited in the specification are herein incorporated by reference in their entirety. Although the foregoing invention has been described in some detail by way of illustration and example, it will be readily apparent to those of ordinary skill in the art in light of the teachings of this invention that certain changes and modifications may be made thereto without departing from the spirit or scope of the appended claims.

What is claimed is:
1. A method of treating small cell lung cancer (SCLC) in a subject comprising a first step of administering to the subject a combination therapy which comprises 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1(2H)-one, and a platinum based antineoplastic agent, and a second step of administering to the subject a monotherapy of 5,8-dichloro-2-[(4-methoxy-6-methyl-2-oxo-1,2-dihydro-pyridin-3-yl)methyl]-7-[(R)-methoxy(oxetan-3-yl)methyl]-3,4-dihydroisoquinolin-1

(2H)-one, wherein the second step does not include administering to the subject said platinum based antineoplastic agent.

2. The method of claim 1, wherein the subject is a human.

3. The method of claim 1, wherein the small cell lung cancer is classified as extensive stage disease.

4. The method of claim 1, wherein the subject is treatment naive.

5. The method of claim 1, wherein the platinum based anti-neoplastic agent is selected from the group consisting of cisplatin and carboplatin.

6. The method of claim 5, wherein the platinum based anti-neoplastic agent is cisplatin.

7. The method of claim 5, wherein the platinum based anti-neoplastic agent is carboplatin.

8. The method of claim 1, wherein the second step of monotherapy is maintained for at least three weeks.

* * * * *